(12) United States Patent
Kim

(10) Patent No.: US 8,685,028 B2
(45) Date of Patent: Apr. 1, 2014

(54) RECIPROCATING SURGICAL SAWS WITH BLADE ASSEMBLIES

(75) Inventor: Chong Chol Kim, Los Angeles, CA (US)

(73) Assignee: Infinesse Corporation, Los Angeles, CA (US)

(*) Notice: Subject to any disclaimer, the term of this patent is extended or adjusted under 35 U.S.C. 154(b) by 247 days.

(21) Appl. No.: 13/156,168

(22) Filed: Jun. 8, 2011

(65) Prior Publication Data

US 2012/0143196 A1    Jun. 7, 2012

Related U.S. Application Data

(63) Continuation-in-part of application No. 12/545,583, filed on Aug. 21, 2009.

(51) Int. Cl.
*A61B 17/00*    (2006.01)

(52) U.S. Cl.
USPC .......................................................... 606/82

(58) Field of Classification Search
USPC ........ 606/79–85, 177; 30/303, 304, 351, 369, 30/503.5
See application file for complete search history.

(56) References Cited

U.S. PATENT DOCUMENTS

| | | | | |
|---|---|---|---|---|
| 2,594,997 A | * | 4/1952 | Ringgold | 30/369 |
| 2,659,969 A | * | 11/1953 | Merkur | 30/369 |
| 3,554,197 A | | 1/1971 | Dobbie | |
| 3,978,862 A | | 9/1976 | Morrison | |
| 4,458,421 A | * | 7/1984 | Lew | 30/369 |
| 4,625,405 A | | 12/1986 | Hudnutt et al. | |
| 5,016,356 A | | 5/1991 | Trench | |
| D326,400 S | | 5/1992 | Fushiya et al. | |
| 5,193,280 A | * | 3/1993 | Jackson | 30/350 |
| 5,201,749 A | | 4/1993 | Sachse et al. | |
| 5,263,972 A | | 11/1993 | Evans et al. | |
| 5,265,343 A | | 11/1993 | Pascaloff | |
| 5,473,820 A | * | 12/1995 | Neubert et al. | 30/386 |
| 5,846,244 A | | 12/1998 | Cripe | |
| 6,007,541 A | * | 12/1999 | Scott | 606/82 |
| 6,022,353 A | * | 2/2000 | Fletcher et al. | 606/79 |

FOREIGN PATENT DOCUMENTS

CA    483135    5/1952

OTHER PUBLICATIONS

Stryker, The Stryker Precision Oscillating Tip Saw, Brochure, Literature No. 9100-001-044 Rev.A, Accessed May 12, 2010, http://www.stryker.com/stellent/groups/public/documents/web_prod/007120.pdf, pp. 1-2.

(Continued)

*Primary Examiner* — Nicholas Woodall
(74) *Attorney, Agent, or Firm* — SoCal IP Law Group LLP; Michael D. Harris

(57) ABSTRACT

The reciprocating saw has two, superimposed, blades having a common axis and arcuate cutting surfaces adjacent each other. Part of one blade extends through an opening in the other blade so that the cutting edge of an upper blade is under the cutting edge of a lower blade. The blades' cutting edges extend around the blade or along a smaller arc. A linkage in the saw converts rotary motion of a motor into synchronous, counter-reciprocating motion of the blades about the axis. Counter-reciprocation minimizes action/reaction forces, which occur when a single reciprocating saw blade changes directions.

25 Claims, 16 Drawing Sheets

(56) References Cited

OTHER PUBLICATIONS

Medical Product Guide, 7600 Oscillating Saw, web-site accessed on May 12, 2010, http://www.medicalproductguide.com/bguide/User/Product/brief/2125/7600-Oscillating-Saw.
Brasseler USA Surgical Power 7 Accessories, Brasseler Orthopaedic Power System, Brochure, Accessed on May 12, 2010, http://www.brasselerusamedical.com/PDFs/BM_2913.pdf, pp. 1-28.
Requirement for Restriction/Election, mail date Jul. 25, 2012, for U.S. Appl. No. 12/545,583, pp. 1-8.
Requirement for Restriction/Election, response filing date Aug. 16, 2012, for U.S. Appl. No. 12/545,583, pp. 1-15.
Non-final Office Action, mail date Oct. 4, 2012, for U.S. Appl. No. 12/545,583, pp. 1-14.
Non-final Office Action, response filed Dec. 24, 2012, for U.S. Appl. No. 12/545,583, pp. 1-16.
Final Office Action, mail date Feb. 28, 2013, for U.S. Appl. No. 12/545,583, pp. 1-8.
Final Office Action, response filed Apr. 23, 2013, for U.S. Appl. No. 12/545,583, pp. 1-19.
Advisary Action, mail date May 2, 2013, for U.S. Appl. No. 12/545,583, pp. 1-3.
Advisary Action, response filed May 20, 2013, for U.S. Appl. No. 12/545,583, pp. 1-15.
Non-final Office Action, mail date Jan. 25, 2010, for U.S. Appl. No. 11/959,437, pp. 1-11.
Non-final Office Action, response filed Apr. 26, 2010, for U.S. Appl. No. 11/959,437, pp. 1-6.
Final Office Action, mail date Aug. 2. 2010, for U.S. Appl. No. 11/959,437, pp. 1-9.
Amendment in Response to Ruling on Petition for Late Priority Claim Response to Jan. 25, 2010 Office Action, response filing date Oct. 1, 2010, for U.S. Appl. No. 11/959,437, pp. 1-8.
Advisory Action Before the Filing of an Appeal Brief, mail date Oct. 20, 2010, for U.S. Appl. No. 11/959,437, pp. 1-2.

* cited by examiner

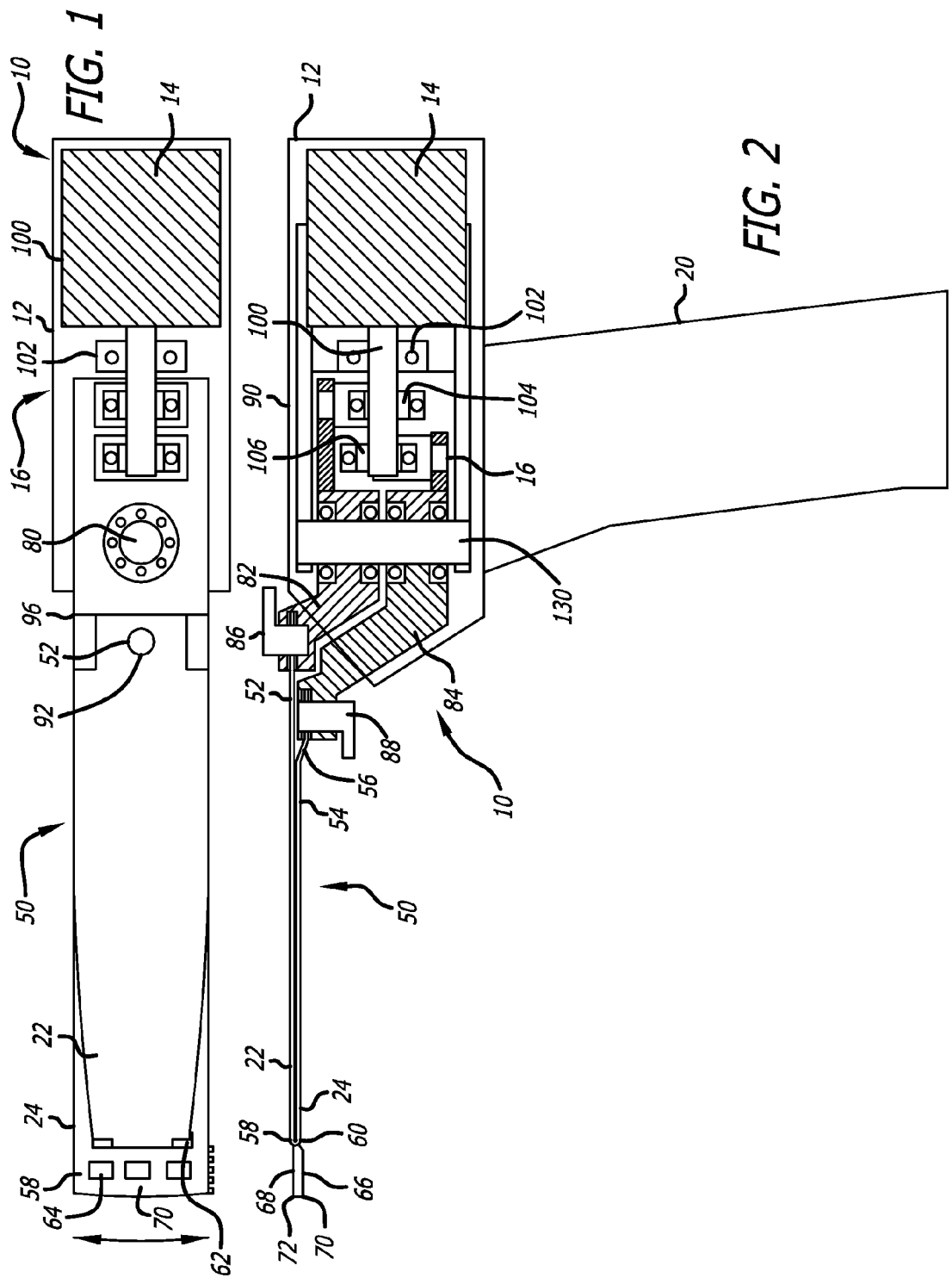

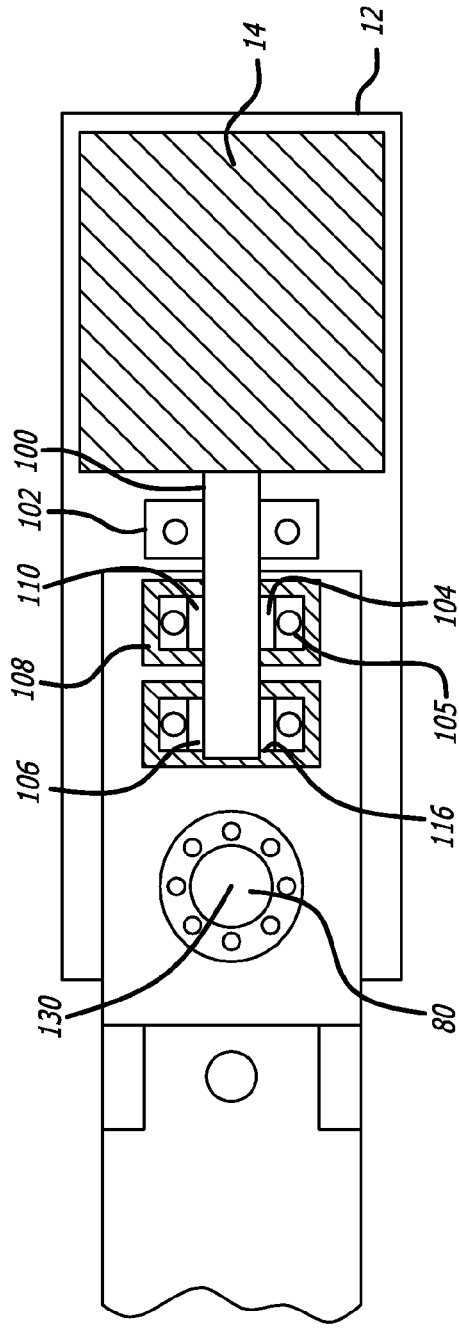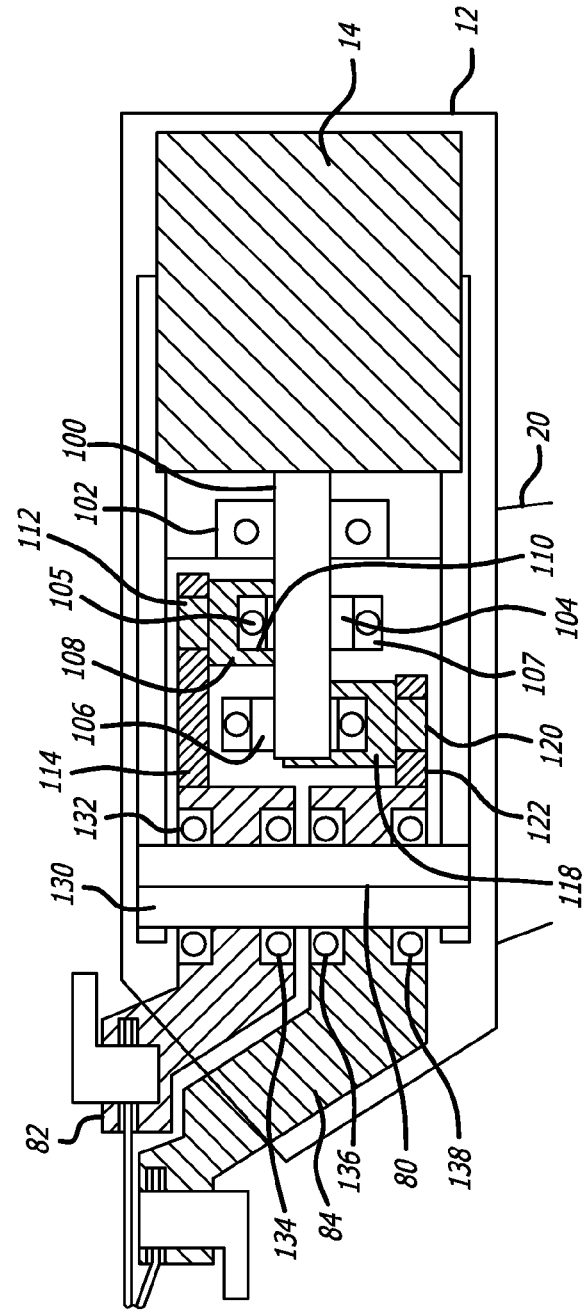
FIG. 3
FIG. 4

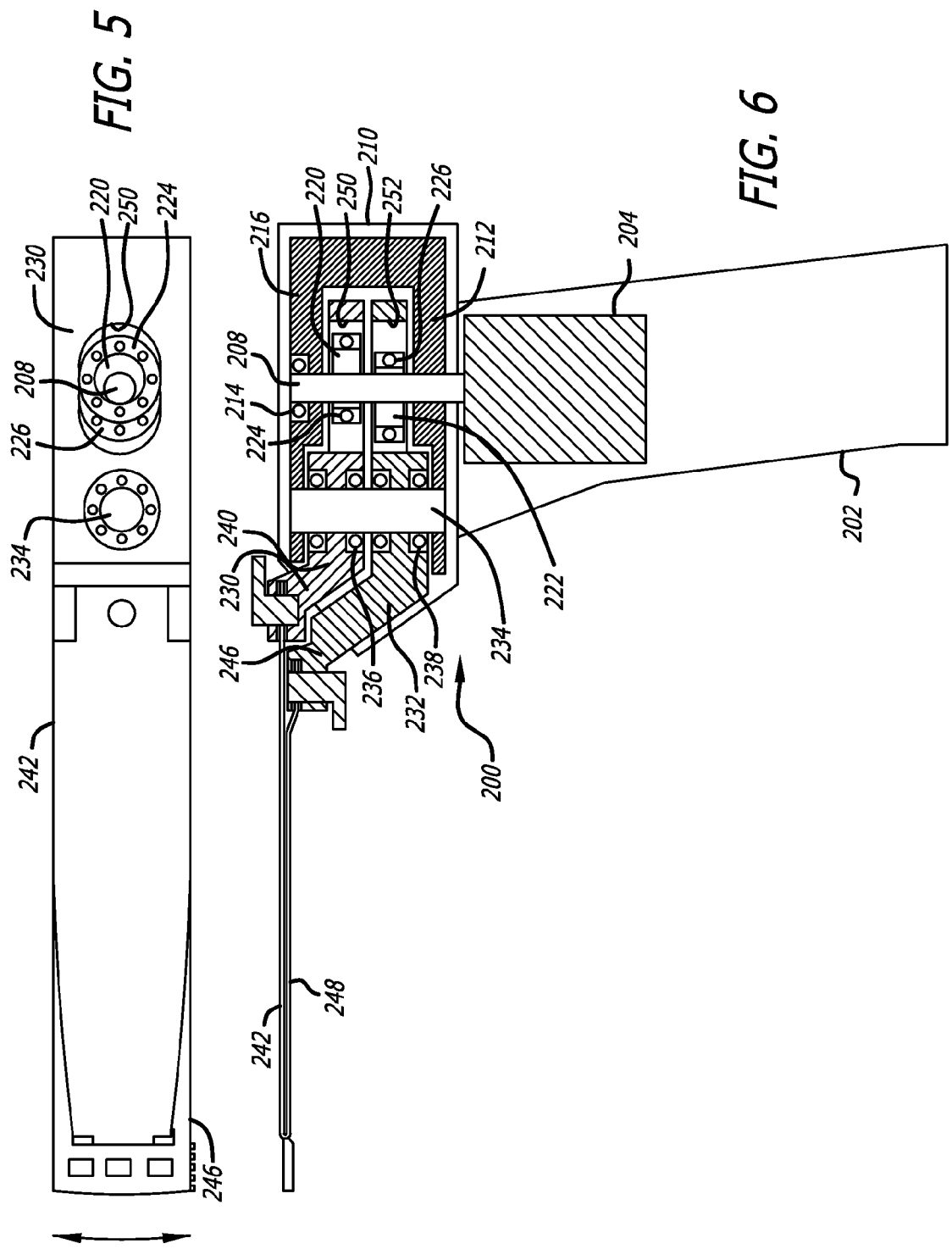

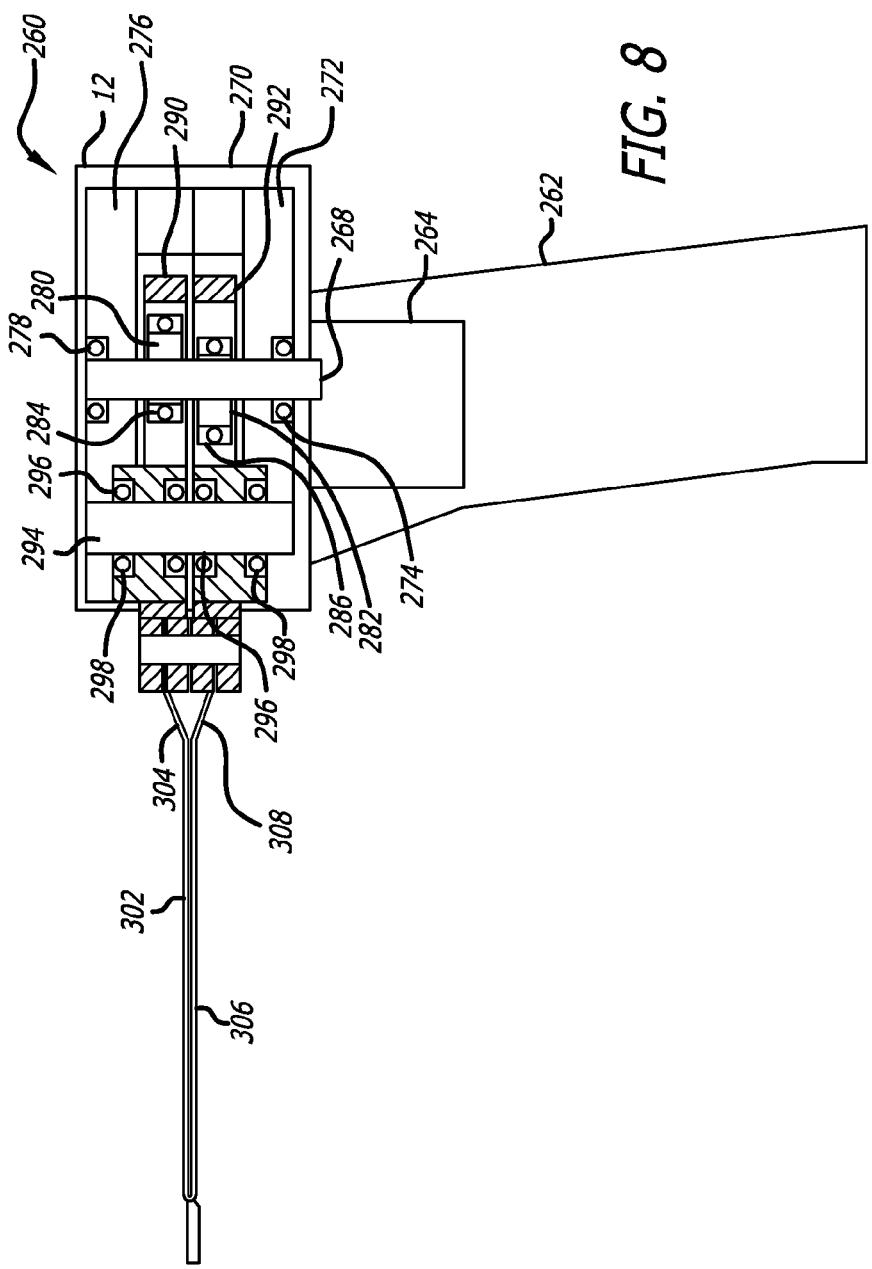
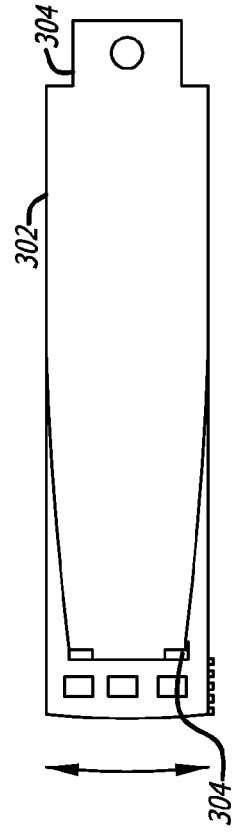

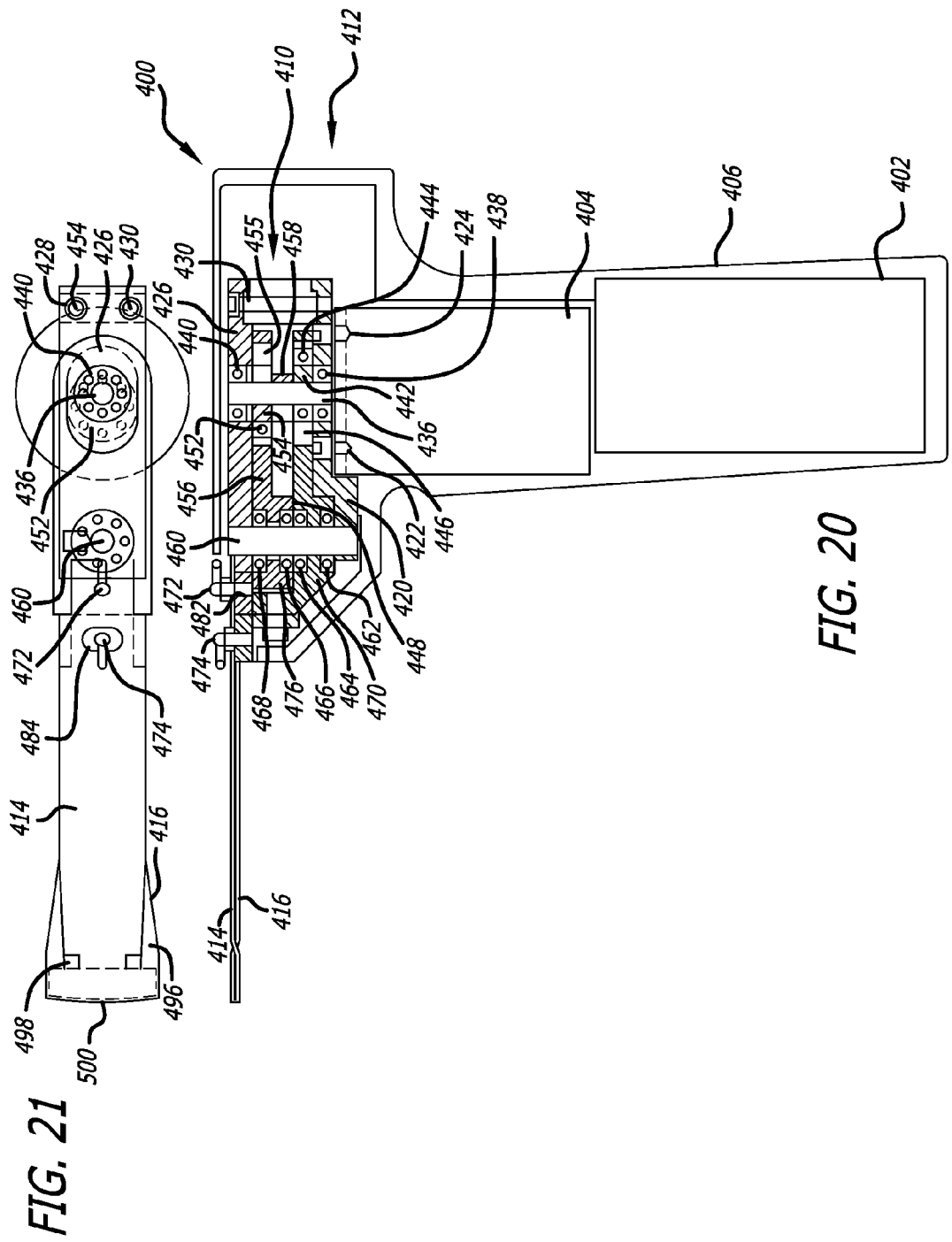

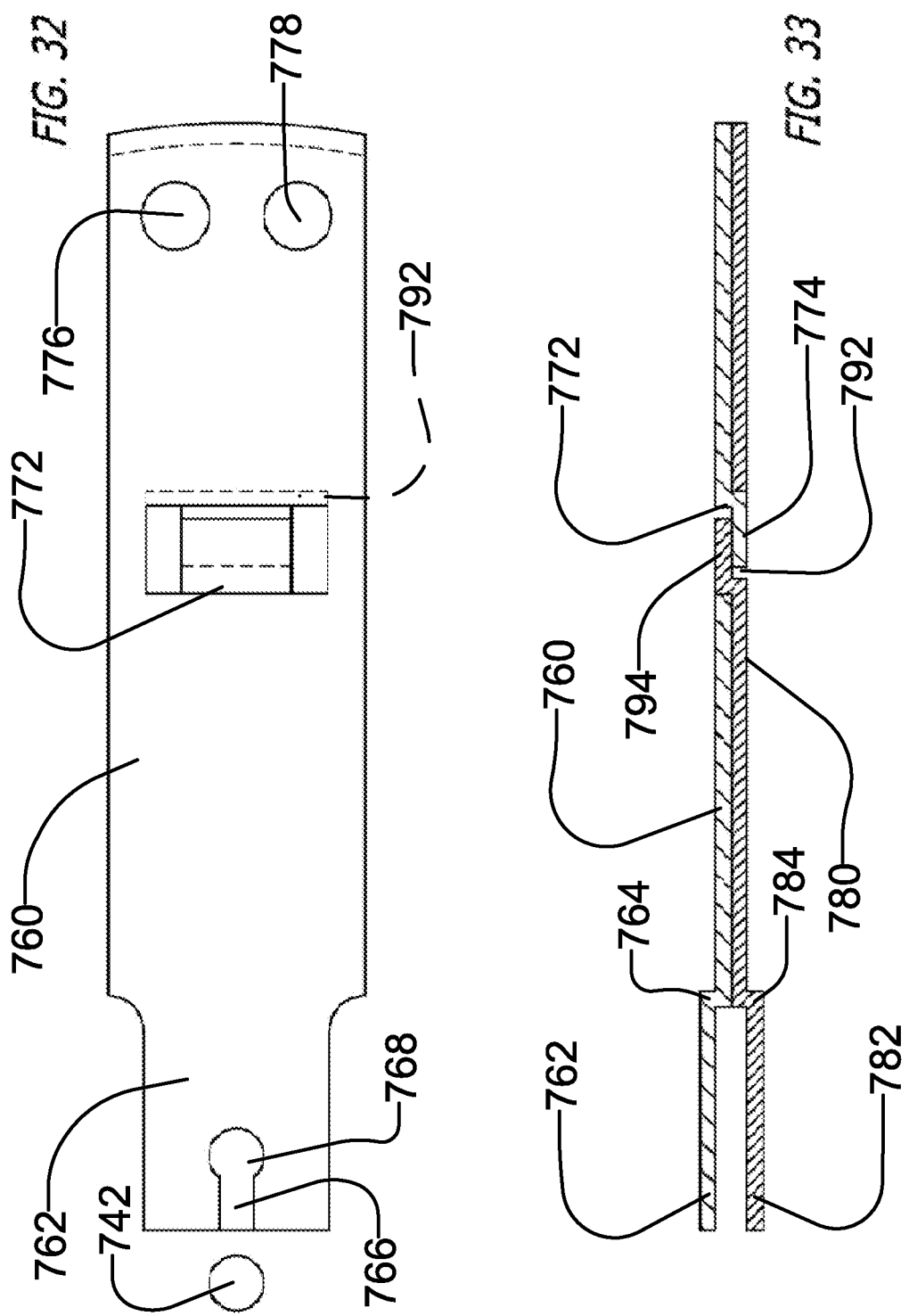

RECIPROCATING SURGICAL SAWS WITH BLADE ASSEMBLIES

RELATED APPLICATION

This application is a continuation-in-part of application Ser. No. 12/545,583 filed Aug. 21, 2009.

BACKGROUND

1. Field of Technology

Precision saws primarily for orthopedic surgery and the blade assemblies used in such saws.

2. State of the Art

Precision cutting of bone is a fundamental requirement for orthopedic surgery. Reciprocating or rotating blade saws often are the tools of choice in these applications. Many reciprocating tools use single, narrow blades with cutting teeth along curved cutting edges. The blades reciprocate over a small arc. One drawback: the single reciprocating blade creates undesirable action/reaction forces. As the blade reciprocates in one direction, forces from the bone to the blade and through the tool to the surgeon's hand push in one direction on the hand. When the blade reverses direction, forces on the surgeon's hand also reverse direction and vibrate his or her hand. The alternating directional forces or vibrations makes controlling the cutting edge's position and movement more difficult.

Ideally, cutting should be controlled, two-directional chipping in which bone removal approximates the width of the cutting blade. Without proper control, however, the blade can move out of the desired two-dimensional cutting plane. The cutting tip, which is where the cutting edge of the blade contacts the bone, essentially vibrates in three dimensions. Bone cutting becomes a more violent chipping into and out of the ideal cutting plane.

Even circular saw blades that rotate in one direction create problems because reaction forces are difficult to control. As the surgeon contacts bone or other tissue or changes the applied forces, the reaction forces on the blade change. The variable reaction forces cause loss of cutting control.

The geometries of conventional cutting blades limit cutting to a small front arc of the blade. As the arc through which cutting takes place increases, the effect of the action/reaction forces also increases. However, using a small arc limits cutting to areas that the cutting surface of the blade conveniently reaches. Other bones or tissue adjacent the bone being cut may block the cutting surface from reaching the cutting zone.

Some problems with using blades with a small arc stems from the problem of the forces on a single blade. Overcoming the single-blade problem could make small-arc blades more viable.

Instead of using a single reciprocating blade, these saws use two, counter-reciprocating blades. The saws may use three blades, with the top and bottom ones reciprocating together and the center one counter-reciprocating with the top and bottom ones.

Two-bladed electric carving knives for carving meat, poultry and other food are well known. They provide substantial control and fast cutting. Typical electric carving knives have two flat, usually serrated, blades that reciprocate along the plane of the cutting surface. As one blade moves outward, the other blade moves inward. Most have some mechanism for holding the blades together while they reciprocate.

Cripe, U.S. Pat. No. 5,846,244 (1998), discloses a counter-reciprocating surgical saw in which the saw teeth move in an arc.

For quality cutting of bone along a single plane, the counter-reciprocating blades should stay together, but they naturally vibrate apart especially while cutting bone. When the blades move apart, they fail to make a single cut in a controlled plane. In addition, cut bone enters the space between the blades, which keeps the blades apart and interferes with cutting.

Familiarly shaped saw housings such as the common pistol shape can accommodate mechanisms for reciprocating the blades. Many reciprocating mechanisms vibrate and make noise. Vibrations tend to move the blade assembly during cutting, which makes controlled cutting more difficult. Vibrations and their noise also are tiring to surgeons and can cause injury to surgeons' hands over time. In addition, running quietly during surgery can be important because loud noises are draining to the operating room staff and to patients if they are awake.

SUMMARY

Applicant's reciprocating saw has a pair of generally planar and superimposed blades. Each blade has a cutting edge that is circular or is an arc of a circle. The cutting edge of one blade is adjacent to the other blade's cutting edge, and the blades reciprocate about an axis of rotation. A pin may extend through the blades at the axis to secure the blades to each other.

The system's geometry is such that the cutting blades reciprocate with equal but opposite angular velocities about the common axis. Therefore, the blades accelerate and decelerate together. The force that each blade transmits to the bone or other material being cut is directly opposite to the force that the other blade exerts. These forces, therefore, cancel or nearly cancel each other so that the bone or other material transmits minor forces back to the combined blades.

Some blades are relatively large and have circular cutting edges that extend more than 180° about each blade. That feature allows surgeons to change directions of the cutting action without having to reposition the handle portion of the tool. The surgeon can make an initial cut pushing the tool forward and then pivot the tool so that the blades cut to the side. This gives the surgeon substantial leeway in avoiding obstacles to cutting in a particular direction.

Other blade assemblies have narrower blades. They project outward from the housing on the pistol-shaped tool. The blades may be aligned with the top surface of the housing. Therefore, surgeons can use the housing and blades as a sight to position the blades' cutting edges.

The mechanisms that reciprocate the blades convert rotary motion from a motor shaft into blade reciprocation. In one saw in which the motor is behind the mechanism and the motor shaft is parallel to the blades, the motor shaft rotates eccentrics in contact with fittings attached to arms on which the blades mount. The fittings pivot on the arms to compensate for the arcuate movement of the fittings as the arms reciprocate. Pivoting allows smoother contact between the eccentrics and fittings.

Mounting the motor below the blade reciprocating mechanism may provide better balance to the saw. In addition, the reciprocating mechanism may operate smoothly without excess vibration.

BRIEF DESCRIPTION OF THE DRAWINGS

FIG. 1 is a top view in section of a first reciprocating saw and blade assembly.

FIG. 2 is a side view, partially in section, showing the first reciprocating saw and blade assembly.

FIG. 3 is an enlarged view of a portion of FIG. 1.

FIG. 4 is an enlarged view of a portion of FIG. 2.

FIG. 5 is a top view in section of another reciprocating saw and blade assembly.

FIG. 6 is a side view, partially in section, showing the FIG. 5 saw and blade assembly.

FIG. 7 is a top view in section of the blade assembly that can connect to the FIG. 8 saw and blade assembly.

FIG. 8 is a side view, partially in section, showing the FIG. 7 saw and blade assembly.

FIG. 20 is a side view partially in section of another reciprocating saw and blade assembly.

FIG. 21 is a plan view, partially in section, of the FIG. 20 saw and blade assembly.

FIG. 32 is a plan view of the blade assembly of FIG. 31.

FIG. 33 is a side view of the blade assembly of FIG. 31.

DETAILED DESCRIPTION

Figure 9:
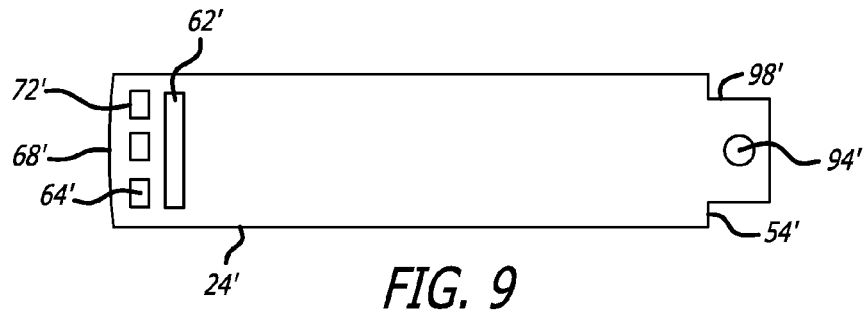
FIGS. 9 and 10 are plan views of blades that can be used in the saw.

Applicant's cutting tool includes at least two, generally planar, superimposed blades. The motor and linkage, which reciprocate the blades in opposite directions, also are explained.

The various mechanisms show several ways to reciprocate the blade assembly. They convert rotary motion from a motor into reciprocating motion. However, insofar as other devices exist for converting motor rotation into blade reciprocation, one of ordinary skill can modify those devices to accept the blade assemblies.

FIGS. 1 and 2 Saw-Motor Mounted Horizontally:

The FIGS. 1 and 2 saw is an example of a device that can reciprocate two blades in opposite directions. Saw 10 may be pistol-shaped because many surgeons favor that shape. With a pistol shape, the surgeon holds the handle, and the blades project horizontally from a housing above the handle. Nevertheless, other shapes with or without pistol grips can be acceptable.

Saw 10 in FIGS. 1 and 2 includes a housing 12 that mounts motor 14 and the mechanism 16 that reciprocates the blades 22 and 24. In FIGS. 1 and 2, the motor is behind the reciprocating mechanism and has a horizontal shaft 100 connecting the motor to the reciprocation mechanism. In this saw, the motor can connect directly to the reciprocating mechanism though a motor shaft, but an intermediate transmission could change the output of the motor.

Handle 20 under the housing holds a battery (not shown) that connects electrically to the motor. Though battery power is optional, and the saw could connect to available AC or DC power, the portability that batteries provide may be desirable. By mounting the motor outside the handle, the handle can accommodate a larger, more powerful and longer-lasting battery. The handle may have an electrical connection for recharging the battery. A door or other opening may allow a connection to a battery charger to charge the battery or supply power to the motor.

Motor location is the primary difference between saw 10 in FIGS. 1 and 2 and the saws of FIGS. 5 and 6 and FIGS. 7 and 8 in which the motor mounts in the handle below the drive mechanism as discussed in more detail.

Blade Assemblies for the FIGS. 1 and 2 Saw and Blade Assembly:

Before discussing the reciprocating mechanisms, the blade assemblies for the FIGS. 1 and 2 saw are discussed. FIGS. 1 and 2 show the two blades, first blade 22 and second blade 24, of blade assembly 50. The blades are superimposed. Both blades are thin so that the assembly is thin even with two superimposed blades. Reducing total blade thickness creates thinner and more precise cuts. Nevertheless, the blades must be thick enough to withstand the stresses from cutting.

Figure 10:
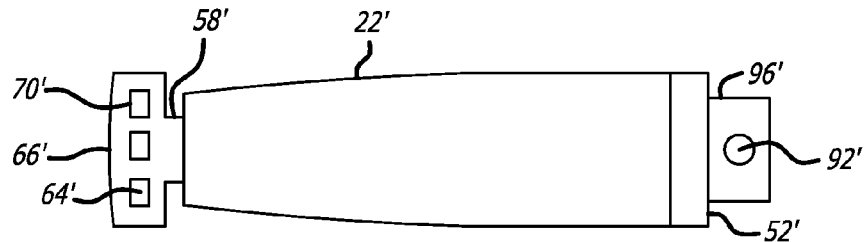

Upper blade 22 in FIG. 2 is longer than lower blade 24 because of the drive mechanism's construction. The blades in the FIGS. 7 and 8 saw are the same length, and FIGS. 9 and 10 shows same-length blades separately. The discussion of the blades in FIGS. 1 and 2 references the blades in FIGS. 9 and 10 even though the latter blades are the same length. However, FIGS. 9 and 10 uses the same reference numerals used with FIGS. 1 and 2. However, in FIGS. 9 and 10, an apostrophe follows the numeral.

The blades in the blade assemblies including those in FIGS. 1 and 2 overlap. Instead of the entire surface of the upper and lower blades being planar with all of the upper blade being above all of the lower blade, the proximal end of the upper blade is above the proximal end of the lower blade, and the distal end of the upper blade is below the proximal end of the lower blade.

In FIGS. 1 and 2, first or upper blade 22 extends from its proximal end 52, and second or lower blade 24 extends from its proximal end 54. As FIG. 2 shows, the blades remain planar over most of their length. The small bend 56 in lower blade 24 is discussed below. Near its distal end 66, upper blade 22 has a bent, narrowed section 58 that bends or curves downward. FIG. 2. Having a gentle bend may avoid metal weakness that sharp angles might cause. The bend extends through a slot 62 in the lower blade 24, and the lower blade bends upward at the slot so that the slot is angled from the horizontal. Thus, the distal end 66 of upper blade 22 is below the distal end 68 of lower blade 24. Because blades 22 and 24 counter-reciprocate, slot 62 is wide enough to permit narrowed section 58 to move fully in both directions as the slot itself reciprocates in the opposite direction.

The bent, narrowed section 58 and slot 62 may be dimensioned such that the walls of the slot may act on the narrowed section to hold the blades together. A low coefficient-of-friction coating such as Teflon® could be applied to reduce friction between the narrowed section and the slot. Friction-reducing coatings or other friction-reducing strategies could be used on other parts of the blades especially where friction may be a problem.

Blade 22 tapers and becomes narrower distally, but blade 24 may be more rectangular. Most of blade 24 is below blade 22, and the added width of blade 24 near its distal end supports upper blade 22 as that blade reciprocates along the lower blade's surface.

Although the FIGS. 1 and 2 blade assembly has slot 62 in the lower blade 24 and narrowed portion 58 of the upper blade extending through the slot, the upper blade could have the slot and the lower blade could be bent through the slot. Thus, though slot 62 is in the second, lower blade 24 (FIG. 1), the other blade 22 could carry the slot.

Optional apertures 64 at the distal ends 66 and 68 of the blades (FIG. 1) disperse cut bone fragments and other tissue away from the blades. The blades may be serrated at their cutting edges 70 and 72 for better cutting. Abrasive coatings also may replace the serrations. One could use smooth blades, but they would be less effective or ineffective for cutting bone. To show the depth of cut, the blades also may have indicia such as spaced lines every ¼ inch, 5 mm or some other spacing.

The proximal end 52 of first blade 22 and the proximal ends 56 for second blade 24 attach to respective arms 82 and 84 of the reciprocating mechanism 16. See FIG. 2. Various devices can attach the blades to the reciprocating mechanism. Quick attach-detach clips 86 and 88 may be desirable because they allow one to change the blades quickly during surgery. Attach-detach clips extend through respective apertures 92 and 94 in the proximal ends of the blade. The blades also have cutouts 96 and 98, FIGS. 1, 9 and 10, to engage mating structure on the arms. In any event, the blade/arm connection should be strong enough to secure the blades to the saw's drive mechanism when the blades are subjected to forces occurring during cutting of bone.

Clips 86 and 88 could be spring loaded to extend into apertures 92 and 94 to secure blades to the reciprocating mechanism. Many other mechanisms such as spring-loaded plates or cams could hold the blades in place. If quick release and replacement may be unimportant, screws, bolts or other fittings could secure the blade to the saw.

Some hospitals and surgeons seek to use disposable mechanical tools to avoid perceived potential problems with using tools more than once. If cost and convenience factors allow, blades 22 and 24 also could attach permanently to drive arms 82 and 84.

FIG. 2 shows blade assembly 50 being parallel with the top 90 of housing 12. Many surgeons prefer that alignment because it allows them to look over the saw and align with the housing and blades to the cutting location—much like firing a pistol. Compare the FIGS. 7 and 8 saw where the blades extend from the vertical center of the saw. To position the blades as shown in FIG. 2, drive arms 82 and 84 angle, but the drive arms in FIGS. 7 and 8 can be straight and project from the center of the housing.

In the FIGS. 1 and 2 saw, the blades reciprocate about axis 80, which is the longitudinal axis of shaft 130 (FIGS. 1-4). The cutting edges 70 and 72 of blades 22 and 24 have profiles that are arcs of a circle, and axis 80 is at the center of that circle. The drive mechanism 16, which is explained in more detail below, pivots the upper blade 22 in one direction about axis 80 while pivoting lower blade 24 in the opposite direction. As a result, cutting edge 70 applies a cutting force on the bone in one direction as cutting edge 72 applies an equal or comparable cutting force on the bone in the opposite direction. The balancing of the forces limits vibrations and makes controlling the cutting tool easier.

Drive Mechanism for FIGS. 1 and 2 Saw:

The drive mechanism 16 in the FIGS. 1 and 2 saws operate as follows. Motor 14 rotates shaft 100. The shaft extends through bearing 102 and eccentrics 104 and 106. See FIGS. 3 and 4. Eccentric 104 rotates within bearing 105 that mounts within fitting 108. The fitting has a U-shaped opening 110 with straight outer walls. The opening receives bearing 105. The top of the fitting (as viewed in FIG. 4) has a short shaft 112 extending upward into arm 114 such that the fitting can pivot relative to the arm. Likewise, eccentric 106 rotates bearing 107 that mounts within a U-shaped opening 116 of fitting 118. A short shaft 120 (FIG. 4), which extends downward from the fitting, engages and pivots on arm 122. Appropriate bearings (not shown) may be provided between short shafts 112 and 120 and their respective arms 114 and 122.

Eccentric 104 acts on its bearing 105 and causes the bearing to act as a cam against the side walls of U-shaped opening 110. Eccentrics 104 and 106 are 180° out of phase. Thus, while fitting 108 moves in one direction, fitting 118 moves in the opposite direction as eccentric 106 acts on its bearing 107, and the bearing acts as a cam pushing a side wall of U-shaped opening 116.

Having the bearings 105 and 107 fit tightly within their respective U-shaped openings and having the eccentrics 104 and 106 fit tightly with their bearings may be important. Otherwise, each eccentric would engage and disengage its bearing or the bearing would engage and disengage its U-shaped opening. The engaging and disengaging generates undesirable vibrations and noise.

Fittings 108 and 118 move in an arc instead of in a plane because the fittings attach to arms 114 and 122, which pivot about shaft 130. Consequently, if the eccentrics and bearings fit too tightly, they would bind as arms 114 and 122 pivoted about shaft 130. Pivoting fittings 108 and 116 in their respective arms 114 or 122 avoids these potential problems. Pivoting allows the eccentrics to remain aligned with the fitting as each shaft moves its arm.

Arms 114 and 122 reciprocate in opposite directions about shaft 130. See FIGS. 3 and 4. The center of the shaft is the axis of rotation of the blades' arcuate cutting surfaces. A pair of bearings 132 and 134 allow arm 82 for upper blade 22 to pivot about the shaft, and bearings 136 and 138 allow arm 84 for lower blade 24 to pivot about the shaft.

Figure 13:
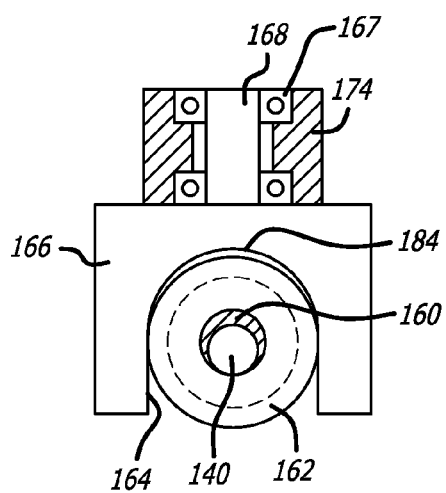
FIGS. 13 and 14 are sectional views taken through planes 13-13 and 14-14 respectively in FIG. 11.
Figure 14:
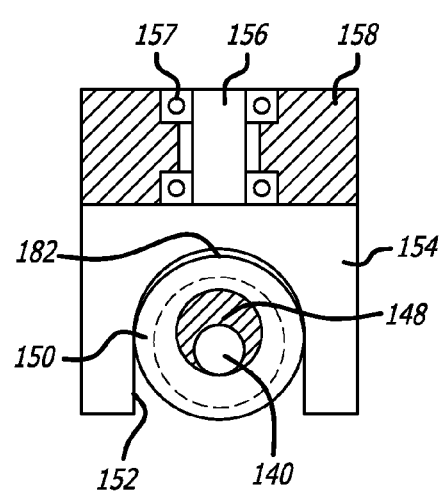
Figure 15:
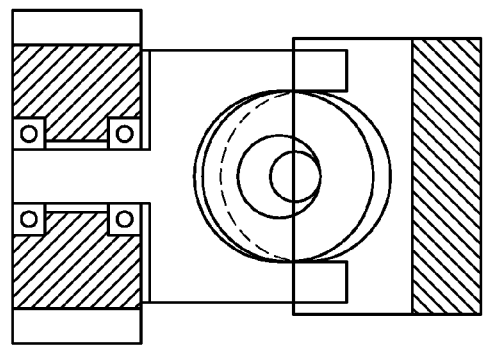
FIG. 15 is a sectional view through FIG. 12.

FIGS. 11-15 Drive Mechanism:

The mechanism that FIGS. 11-15 shows also uses a motor with a horizontal shaft. Shaft 140 extends through bearing 142 on flange 144 projecting upward from base 146. See FIG. 11. The shaft also extends through eccentric 148 in bearing 150 (FIG. 14). The bearing mounts within a U-shaped opening 152 in fitting 154. Fitting 154 has a short shaft 156 opposite the U-shaped opening that extends into bearing 157 in arm 158. As described below, arm 158 connects to arm 176, which connects to an upper blade. See FIG. 11.

Figure 11:
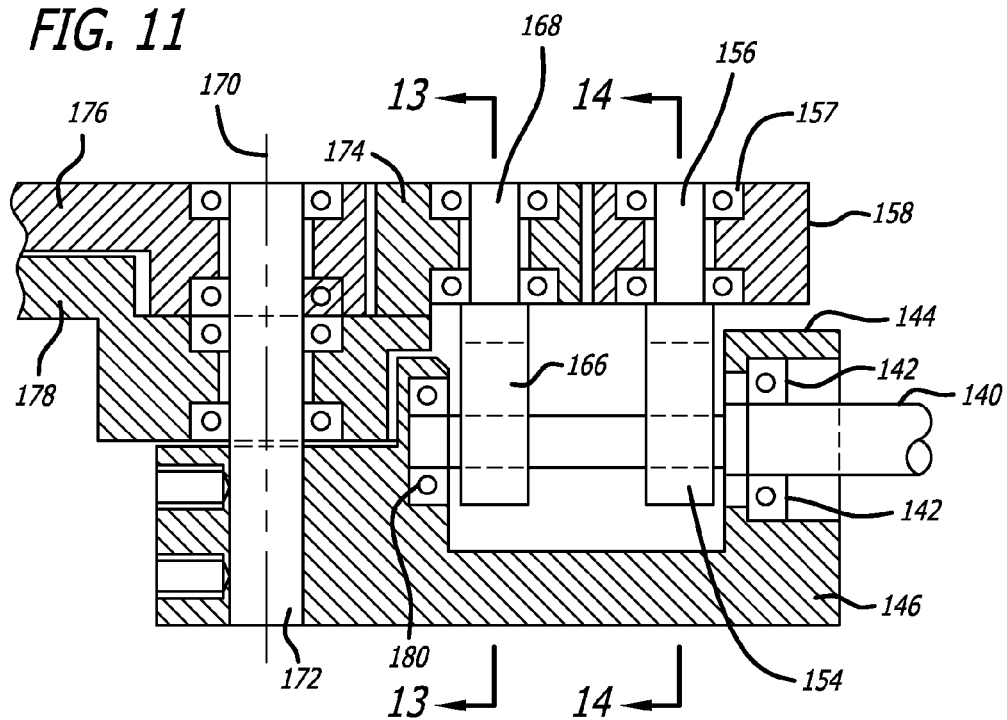
FIG. 11 is a sectional side view of part of a drive mechanism that counterreciprocates blade assemblies.
Figure 12:
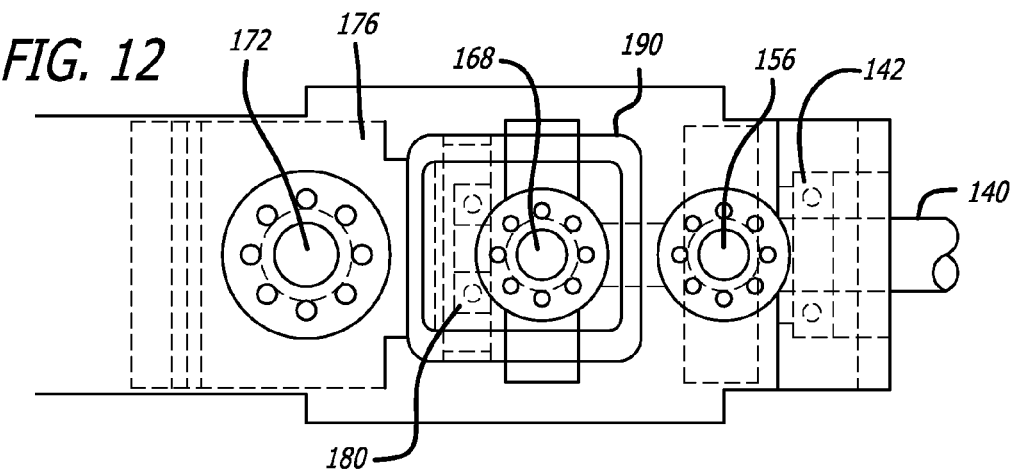
FIG. 12 is a sectional plan view of the FIG. 11 drive mechanism.

As shaft 140 and eccentric 148 rotate, bearing 150 revolves. The horizontal (right and left) component of the movement of bearing 150 moves arm 158 horizontally. See FIGS. 11 and 14. However, arm 158 pivots about axis 170 of shaft 172 rather than moving horizontally in a plane (FIG. 11). If fitting 154 were fixed to arm 158, fitting 154 and bearing 150 would angle with respect to each other, especially at the ends of the fitting's movement. Accordingly, the outside of bearing 150 would have to be smaller than the inside of U-shaped opening 152 to allow for the relative motion. Otherwise, the bearing would bind as the fitting's angle to the bearing changes. However, if the bearing is smaller than the U-shaped opening, it does not remain in constant contact with the fitting. If the bearing releases and engages the fitting, it may generate noise and vibration. By allowing fitting 154 to pivot within arm 158 through the fitting's rotating connection of shaft 156, bearing 150 can remain in contact with inside vertical walls U-shaped opening 152 as arm 158 reciprocates through its path.

After shaft 140 passes though eccentric 148 (FIG. 14), it continues through eccentric 160 and into bearing 180 (FIGS. 11 and 14). Eccentric 160 is within bearing 162 (FIG. 13). Rotation of shaft 140 and eccentric 148 moves bearing 162. U-shaped opening 164 in fitting 166 receives the bearing. Short shaft 168 opposite U-shaped opening 164 is received in bearing 167 in arm 174. Arm 174 connects to or is integral with arm 178 (FIG. 11), which supports a lower blade.

The horizontal (right and left) component of the movement of bearing 162 urges arm 174 in a horizontal arc about shaft 172. For the same reason for having fitting 154 pivot in arm 158, fitting 166 pivots in arm 174.

Small gaps 182 and 184 separate the respective top position of bearing 150 and 162 from the top of their U-shaped opening. Therefore, when the eccentrics move the bearings to the top of their path, the bearing does not contact the top of its U-shaped opening. Contact could cause vibrations and noise.

Eccentric 148 (FIG. 14) has a larger diameter than eccentric 160 (FIG. 13) so that the horizontal movement from bearing 150 acting on fitting 154 is greater than the horizontal component from bearing 162 acting on fitting 166. That is because fitting 166 is closer than fitting 154 to axis of rotation 170. See FIG. 12. Therefore, fitting 154 must move farther than fitting 166 to achieve the same angular movement.

Rectangular ring 190 (may connect the rear (right side in FIG. 12) portion of arm 158 to arm 176. The ring extends around arm 174 (FIG. 11) to prevent contact between the arm and ring.

The dimensions of the various components such as the diameters of eccentrics 148 and 160 and the spacing of the fittings 154 and 166 depend on the size of the housing, the desired angular movement of the blades and other factors. Those of ordinary skill may choose dimensions and spacing of the various components for the desired saw operation.

The FIGS. 5-6 and FIGS. 7-8 Saw and Blade Assemblies:

The motor mounts in the handle below the reciprocating mechanisms in the FIGS. 5-6 and FIGS. 7-8 saws. Referring first to the saw of FIGS. 5 and 6, motor 204 mounts in handle 202 of saw 200 (FIG. 6). A battery (not shown), which supplies power to the motor, also mounts in the handle. The motor rotates shaft 208, which extends upward from the motor through wall 212 into housing 210. Bearing 214 in wall 216 also supports the motor shaft.

Eccentrics 220 and 222 connect to shaft 208. The eccentrics are within respective bearings 224 and 226. As FIG. 6 shows, the eccentrics and bearings are 180° out of phase. Each bearing 224 and 226 mount in the rear (right in FIGS. 5 and 6) of respective arm 230 and 232. Shaft 234, which extends between walls 212 and 216, support arms 230 and 232. See FIG. 6. Each arm has a pair of bearings 236 and 238 permitting the support arms to reciprocate about shaft 234.

Arm 230 bends upward at 240, and the proximal end (right in FIG. 6) of upper blade 242 connects to the arm. Similarly, arm 232 bends upward at 246 where it connects to the proximal end of lower blade 248. The blades in FIGS. 5 and 6 may be the same as or similar to the blades used in the FIGS. 1 and 2 saw. Therefore, they are not discussed in detail.

Eccentrics 220 and 222 and bearings 224 and 226 acting on respective support arms 230 and 232 reciprocate blades 242 and 248. As motor shaft 208 rotates eccentric 220, the outside of bearing 224 acts on cam surface 250 (FIG. 5) of arm 230 to cause the arm to reciprocate about shaft 234. Likewise, the motor shaft rotates eccentric 222 so that the outside of bearing 226 cams against surface 252 of arm 232 causing that arm to reciprocate about shaft 234. Because the eccentrics are 180° out of phase, the arms counter-reciprocate—arm 230 pivots in one direction while arm 232 pivots in the opposite direction.

In FIGS. 7 and 8, motor 264 and a battery (not shown) mount in handle 262 of saw 260. The motor rotates shaft 268. Bearings 274 and 278 support the shaft.

Eccentrics 280 and 282 and bearings 284 and 286 act on arms 290 and 292. Rotating shaft 268 rotates eccentrics 280 and 282, which are within respective bearings 284 and 286. Eccentrics 280 and 282 are 180° out of phase. The bearings in which the eccentrics mount are within an appropriately shaped openings of one arm 290 or 292. Shaft 294 supports the arms. See FIG. 8. Each arm has a pair of bearings 296 and 298 permitting the arms to reciprocate about the shaft.

Unlike previously discussed saw and blade assemblies, arms 290 and 292 in the FIGS. 7 and 8 saw have no bend. Accordingly, blade 302 and 306 are centered vertically on the saw. Each blade may have a small bend 304 and 308, respectively, near its proximal end to connect with a respective attachment fitting. The bends at the proximal ends of the blades permit most of blades 302 and 306 to be flat against each other. See FIG. 8

Alternative Blade Design:

The cutting edges 70 and 72 of blades 22 and 24 in FIGS. 1 and 2 and other figures extend through a relatively short arc. In addition, slot 62 is close to the distal 68 end of blade 22. FIGS. 16-19 show another blade assembly in which the slot is more proximal, the cutting surfaces extend about a greater arc and the blades are wider than their counterparts, blades 22 and 24.

FIGS. 16-19 show again how a crossover overlapping design may enhance blade coupling. First or upper blade 320 and second or lower blade 322 (FIGS. 16 and 17) attach to a reciprocating mechanism, which is not shown in those figures. The designation of "upper" and "lower" is different in the discussion of this blade than in the previously described blades. The axis of pivoting of these blades is more distal than the axis for the other blades. For FIGS. 16-19, the upper blade is the blade with the distal portion above the lower blade.

For at least two reasons, the reciprocating mechanism driving the FIGS. 16-19 blade differs from the mechanisms previously described. First, the axis of rotation for the earlier-discussed blades is within the housing close to where the eccentrics act on the arms reciprocating the blades. The axis of rotation is outside the housing for the FIGS. 16-19 blades. Second, the ends of the arms where the eccentrics act in FIGS. 5 and 6 and FIGS. 7 and 8 moved equal angles, so that the blades reciprocated equally. The FIGS. 1 and 2 saw compensates for smaller movement of the rear portion of arm 122 compared to the movement of the rear portion of arm 114 by using a smaller-diameter eccentric 106 than that of eccentric 104. Those of ordinary skill will recognize that when designing the reciprocating mechanism of the FIGS. 16-19 saw and blade assembly, some compensation may be necessary for different reciprocation distances of the mechanism connecting to the blades.

Figure 16:
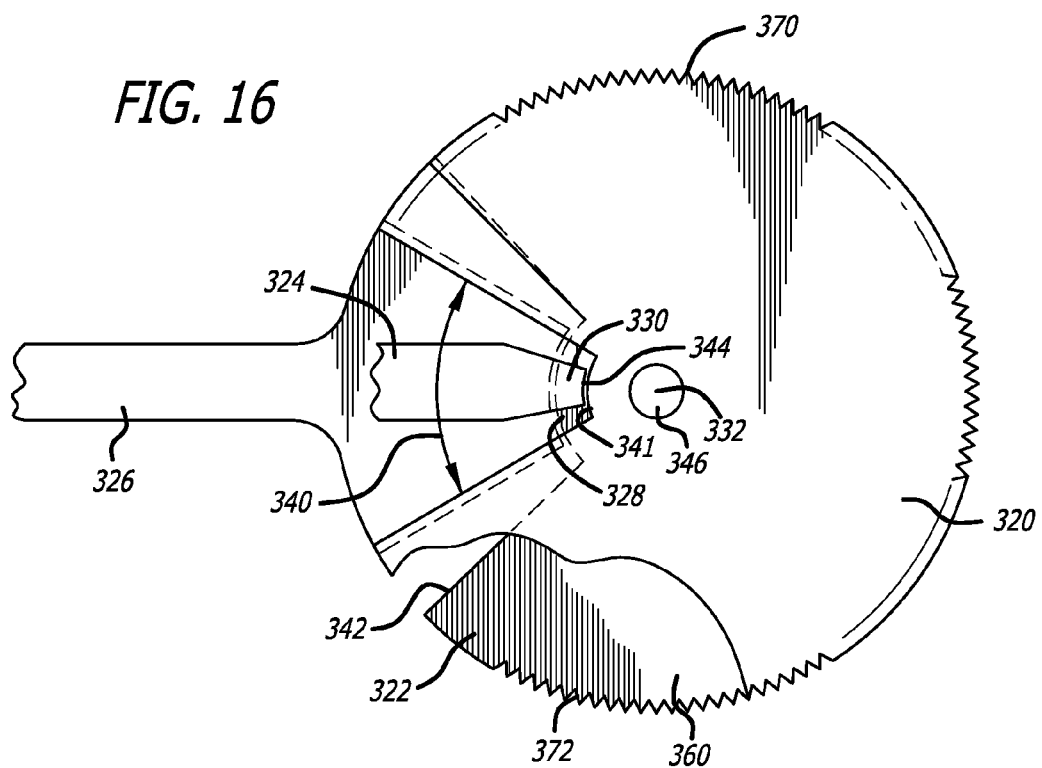
FIG. 16 is a plan, sectional view.
Figure 19:
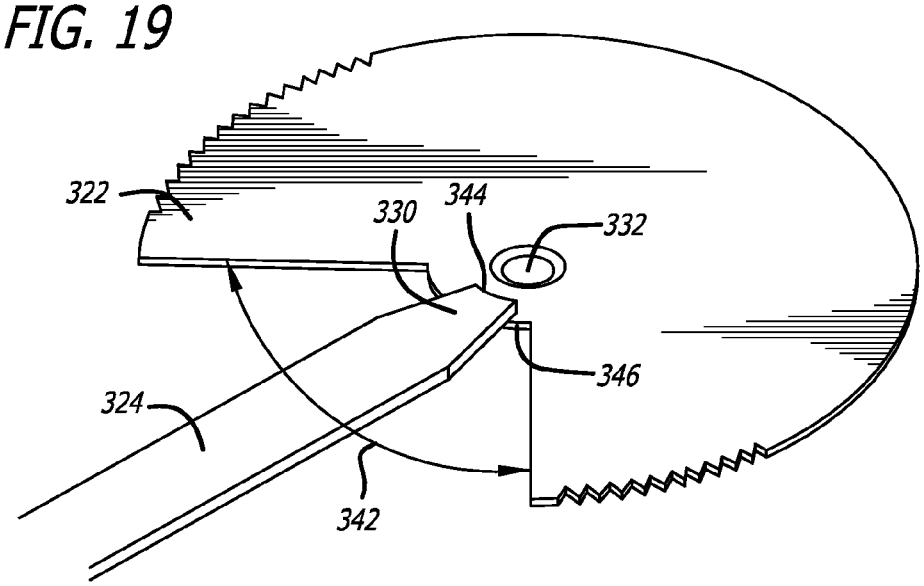

Arm 324 of first or upper blade 320 (FIG. 16) extends though an arc-shaped cutout section 330 of second or lower blade 322. FIG. 16 shows arm 324 entirely through the cutout section in an operating position. The cutout section has a distal, arcuate edge 334 (FIG. 19). Thus, the distal, tapered end 330 of arm 324 is within the cutout section. Distal edge 344 of arm 324 has an arcuate shape with its center at the axis 332 of first blade 320.

The distal end of arm 326 of lower blade 322 tapers outward into plateau 348 (FIGS. 16 and 18), which extends over arc-shaped region 340. The plateau has depending sidewalls 350 and 352 that form the sides of arc-shaped opening 340.

First or upper blade 320 includes an arc-shaped region 342. See FIG. 19. The arc-shaped region occupies a larger arc than wedge-shaped cutout 340 of second blade 320. Compare FIGS. 18 and 19. Inner peripheral edge 346 of first blade 320 is arcuate. The distance from edge 346 to axis 332 (FIG. 19) is greater than the distance from arm 326's distal peripheral edge 327 to the axis.

Blades 320 and 322 can be assembled as follows: The proximal end of arm 324 (left side in FIG. 16), which extends from upper blade 320's cutting region 360, is inserted through arc-shaped opening 330 in lower blade 322 in the space between peripheral edge 346 of the upper blade and the distal edge 344 of plateau 348. See FIGS. 16 and 18. With arm 326 below arm 324, first blade 320 overlaps second blade 322 (FIG. 16). When the blades are positioned together, distal edge 327 of arm 324 abuts inner peripheral edge 334 of second blade 322.

Wedge-shaped cutout 342 of first blade 320 must extend through a sufficiently wide arc to accommodate the reciprocation of plateau 348 of second blade 322 as the blades counter-reciprocate. See FIG. 16.

Figure 17:
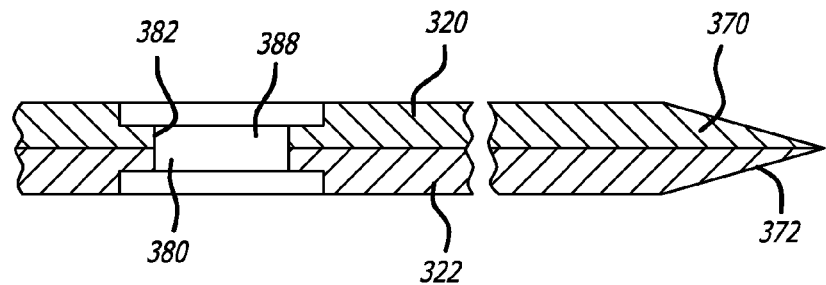
FIG. 17 is a side sectional view of another blade assembly.
Figure 18:
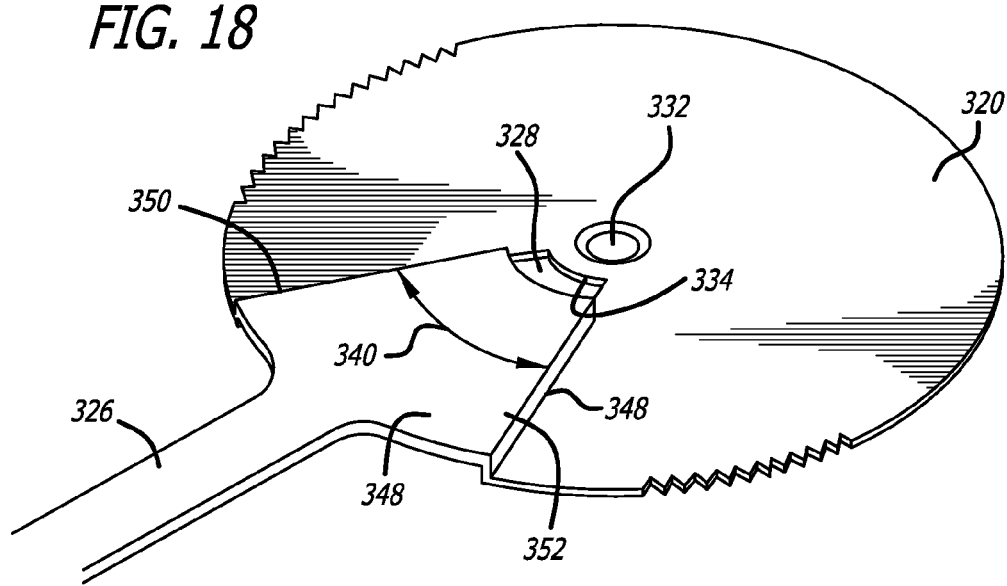
FIGS. 18 and 19 are perspective views of the upper and lower blades, respectively, of the blade assembly of FIG. 16.

The cutting edges 370 and 372 taper and meet at a sharp edge (FIG. 17). Although only FIG. 17 shows tapered cutting edges, blades from the other blade assemblies can be tapered. The edge design directs cut bone and tissue away from the blades. Directing tissue away prevents or minimizes tissue from entering any space between the blades. Tissue between the blades tends to push the blades apart, which can create undesirable thicker cuts with variable thicknesses. In addition, tissue between the blades could interfere with reciprocation. Blades 320 and 322 also could use slots similar to slots 64 shown in FIG. 1 and other figures to expel tissue.

Cutting edges 370 and 372 have appropriate serrations. In FIGS. 16-19, the cutting surfaces and the serrations extend about 220° around the respective cutting regions 360 and 362 of the blades. Extending the cutting surface more than 180° allows surgeons to cut forward, to both sides and backwards without substantially pivoting the entire surgical saw. This can be a useful feature because by choosing a particular portion of the cutting surface, the surgeon can position the tool for cutting while avoiding cutting into adjacent tissue. By pushing forward so that the blade cuts into the bone toward blade axis 332, the surgeon also can make a forward cut as wide as the diameter of the blade assembly.

Nevertheless, depending on the position of the bone and surrounding tissue, a surgeon may want to use narrower or wider blades. Consequently, the blades could use smaller- or wider-diameter cutting portions. Similarly, the cutting portions of the blades could have portions of each blade removed.

The blade assembly design allows cutting portions 360 and 362 to remain in their respective planes without undue bending or separating from each other while the blades counter-reciprocate. The crossover design that FIGS. 16-19 show may be sufficient to hold the blades together without any other attachment. Otherwise, a pin 380 through axis 322 may hold the blades together.

As FIG. 17 shows, pin 380 attaches blades 320 and 322 together. Pin 380 extends through opening 382 at axis 322. Heads 384 and 386 of pin 380 hold the blades together. The heads of the pin could extend above and below the outside surfaces of the blades, but that adds thickness to the blade assembly. Protruding heads likely are undesirable because they may block some deep cuts.

The countersunk pin arrangement shown in FIG. 17 alleviates protruding heads. Opening 382 may be formed to accommodate the countersunk arrangement. Heads 384 and 386 push blades 320 and 322 together. The heads may screw or otherwise attach together, or a mechanism (not shown) may be provided to release one head 384 or 386 from the center section 388 of the pin. Heads 384 and 386 and the structure forming the countersink must be thick and strong enough to avoid breaking or deforming during use.

Instead of having cylindrical regions for opening 382, the bores can be conical, tapering outward toward the top and bottom of the blade. The pin in that blade assembly would have a shape corresponding to the conical walls. Other pin shapes also are possible.

FIGS. 20 and 21 Saw and Blade Assembly:

Saw 400 also may be pistol-shaped in FIGS. 20 and 21. Battery 402 and motor 404 mount conventionally within handle 406. The inside of the handle may have surfaces that secure the motor and battery. A door or other structure (not shown) allows users to remove and replace the battery. A plug or other electrical structure (not shown) may allow outside power to connect electrically to the battery or motor.

Housing portion 412 (upper part of FIG. 20) contains drive mechanism 410 that reciprocates blades 414 and 416 in opposite directions. A trigger (not shown) activates and controls the speed of the drive mechanism by controlling motor 404. Two or more screws 422 and 424 may attach base 420 of the drive mechanism to the top of motor 404. A pair of pins 428 and 430 (FIG. 21) attaches base 420 to upper platform 426. See FIG. 20.

Motor shaft 436 extends through bearing 438 in base 420 and into bearing 440 in upper platform 426. The motor shaft is fixed to lower eccentric 442 and upper eccentric 454, which mount respectively in bearings 444 and 452. The bearings seat in appropriately shaped opening 446 in lower arm 448 and opening 455 in upper arm 456. See FIGS. 20 and 21. The motor shaft also may pass through a spacer 458, which may separate the two eccentrics.

Fixed pivot shaft 460 extends between base 420 and upper platform 426 (FIGS. 20 and 21). The pivot shaft extends though a pair of bearings 462 and 464 in lower arm 448 and through another pair of bearings 466 and 468 in upper arm 456. This mechanism uses four bearings, but using a different number of bearings or other means for decreasing friction is possible. Thus, the upper and lower arms can pivot about pivot shaft 460. The upper and lower arms connect to the cutting blades as discussed below.

The motor shaft's rotation of eccentrics 442 and 454 causes bearings 444 and 452 to cam along the inside surfaces of the openings of arms 448 and 456 so that the arms reciprocate. The eccentrics are offset 180° so that the arms reciprocate in opposite directions. Each arm connects to one of the blades; lower arm 448 connects to blade 416, and upper blade 456 connects to blade 414. Therefore, arm reciprocation reciprocates the blades.

Blade 414 attaches to upper arm 456, and blade 416 attaches to lower arm 448. The lower arm has a distal bent portion 470 that properly positions the lower blade. See FIG. 20. Blades 414 and 416 are aligned with the top of housing portion 412. Though such an alignment is not required, the alignment allows surgeons to sight along the top of the housing and the top of the blade assembly while positioning the blades' cutting edges.

The upper and lower blades can be fastened to the upper and lower arms as desired. In FIGS. 20 and 21, clamps 472 and 474 secure the upper and lower blades 414 and 416 to the respective upper and lower arms. The clamps may extend through openings in each blade's proximal end. Because the clamp holding the lower blade is above the upper blade, the upper blade has an opening through which the lower blade's clamp passes. The opening is discussed further in the discussions of the blades shown in FIGS. 23 and 24. The clamps may have a shape that mates with the shape of the blade opening such that rotating the clamp engages the inside surface of the opening. The clamps also may have structure that prevents their rotation when the clamps fully engage the blade openings. The clamps also could have a circumferential slot that receives the blade openings inside edge when the clamp is rotated into a locked position. The clamps also can have a pad that pinches the proximal end of the blade. Using other clamping structures may be desirable.

Figure 22:
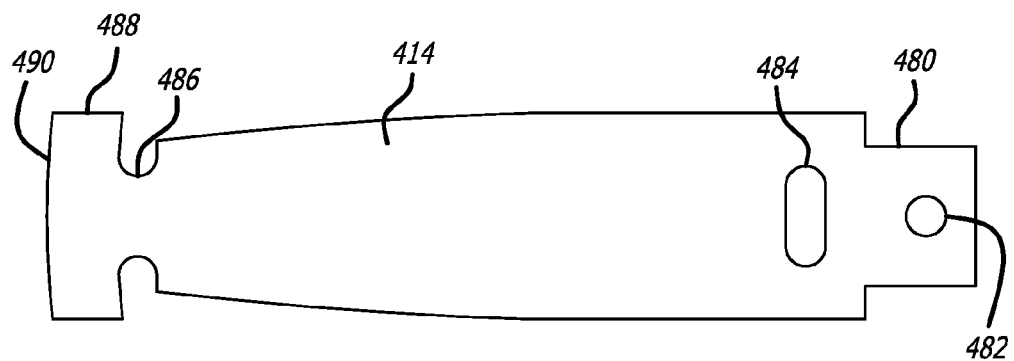
FIGS. 22 and 23 are plan views of the blade that are part of the saw and blade assembly of FIGS. 20 and 21.
Figure 23:
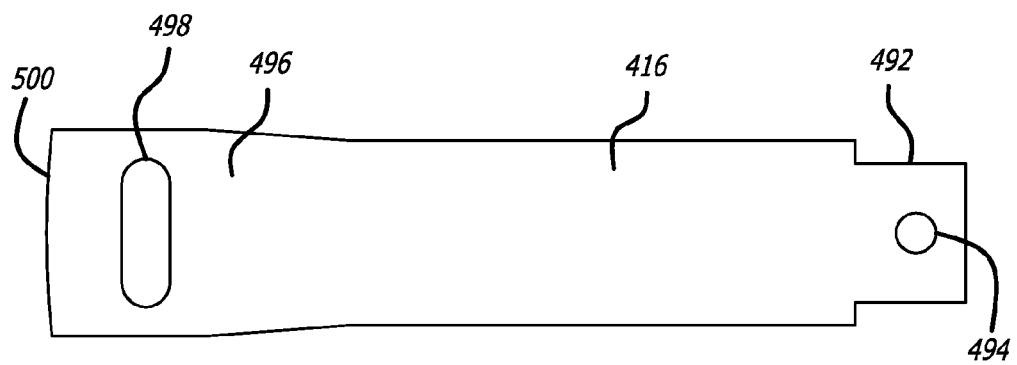

Blades 414 and 416 may be similar to the blades shown in FIGS. 1 and 2. FIGS. 22 and 23 show exemplary blades for the FIGS. 20 and 21 saw. Upper blade 414 has a proximal narrow portion 480, which may engage structure on the upper arm. Opening 482 receives clamp 472. Instead of opening 482 being enclosed, it could be a slot. Elongated opening 484 is spaced from opening 482. The blade's distal end narrows to cutout portion 486, which is narrow enough to fit into slot 498 through blade 416 (FIG. 23). The distal end 488 of blade 414 terminates in an arcuate cutting surface 490.

Lower blade 416 also has a proximal narrow portion 492, which may engage structure on the lower arm. See FIG. 23. Opening 494, which receives its clamp, is aligned with elongated opening 484 in the upper blade. The lower blade has a wider portion 496, and slot 498 is in the wider portion (FIGS. 21 and 23). Arcuate cutting surface 500 aligns with cutting surface 490. The cutting surfaces' arcs are part of a circle whose center is at the longitudinal axis of fixed shaft 460. Optional distal openings near the cutting surfaces may be provided, but FIGS. 22 and 23 show none.

Dimensions can vary and depend on the arc through which the blades reciprocate and the size of the housing. In FIGS. 20 and 21, the length of upper arm 456 may be 2.5 in. (6.4 cm). Some English units are rounded due to converting from fractions to decimals (e.g., ⅝ might round from 0.625 to 0.6), and metric conversions are approximate. The width of the opening in which upper eccentric 454 mounts may be 0.62 in. (15.9 mm). The opening's length may be 1 in. (25.4 mm). The eccentric's diameter may be 0.38 in. (9.5 mm) with a 0.47 in. (11.9) offset from the center of shaft 436. The lower arm's 448 length also may be 2.5 in. (6.4 cm). It may have the same size opening as the opening in the upper arm. The upper arm also has a short extension 476 (FIG. 20) extending distally 0.28 in. (7.1 mm) to where the upper blade 414 attaches.

Blade 414 may be 4 in. (102 mm) long, and blade 416 may be 3.5 in. (89 mm) long. The width of both blades before tapering at the distal ends may be 0.75 in. (19 mm). Slot 498 may be 0.68 in. (17 mm) by 0.19 in. (4.8 mm). The width of each blade's cutting surfaces 490 and 500 may be 0.94 in. (23.8 mm). Each blade may be 0.025 in. (0.64 mm) thick.

Figure 25:
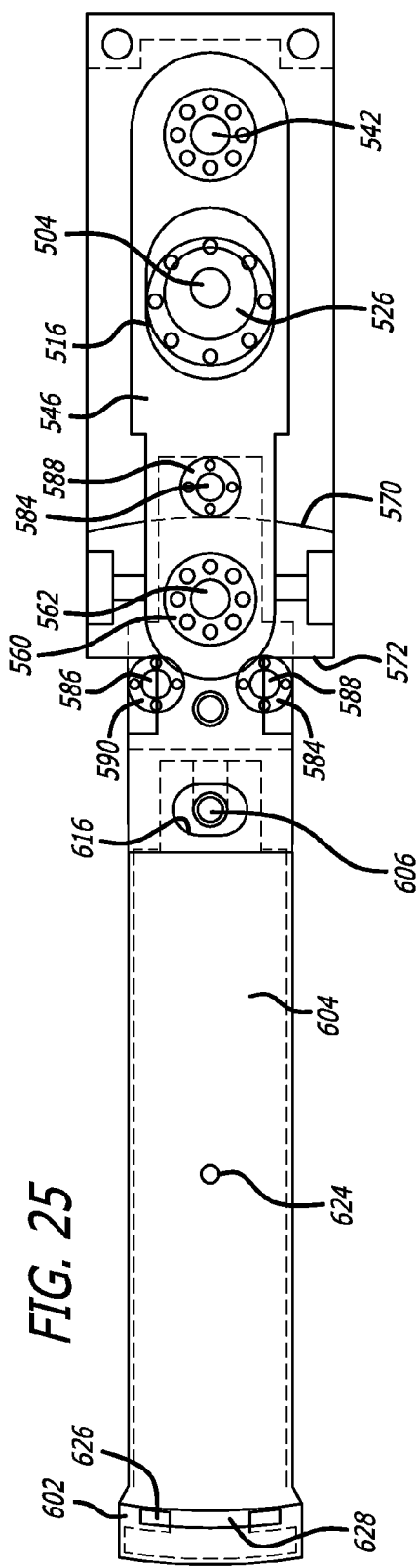
FIG. 25 is a plan view, partially in section, of the FIG. 24 saw and blade assembly.
Figure 24:
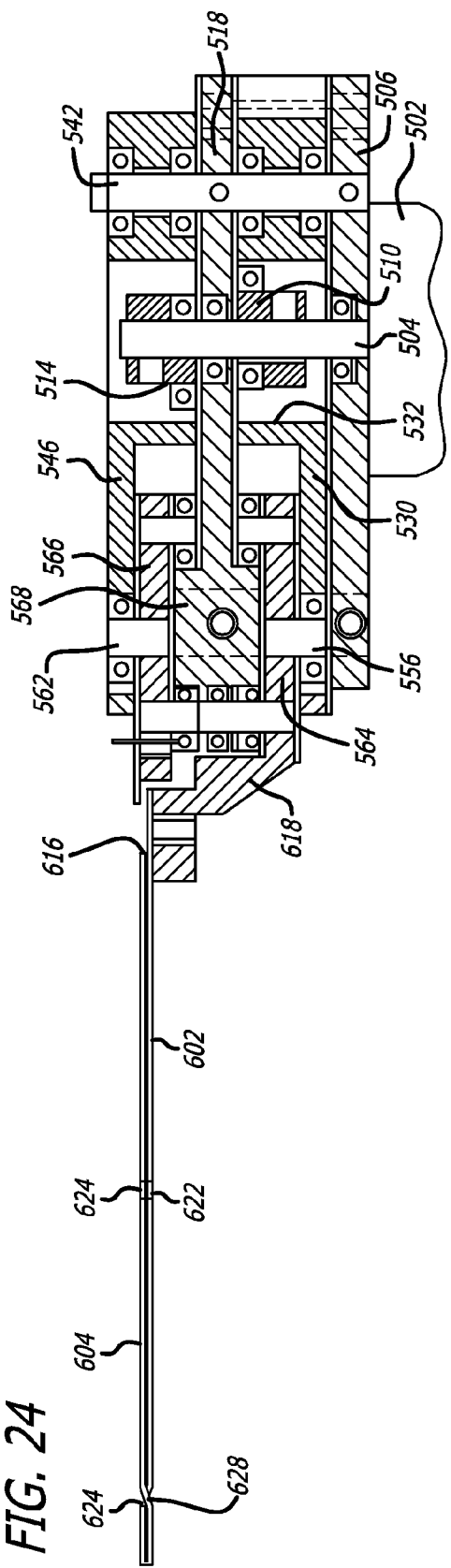
FIG. 24 is a side view partially in section of another reciprocating saw and blade assembly.
Figure 26:
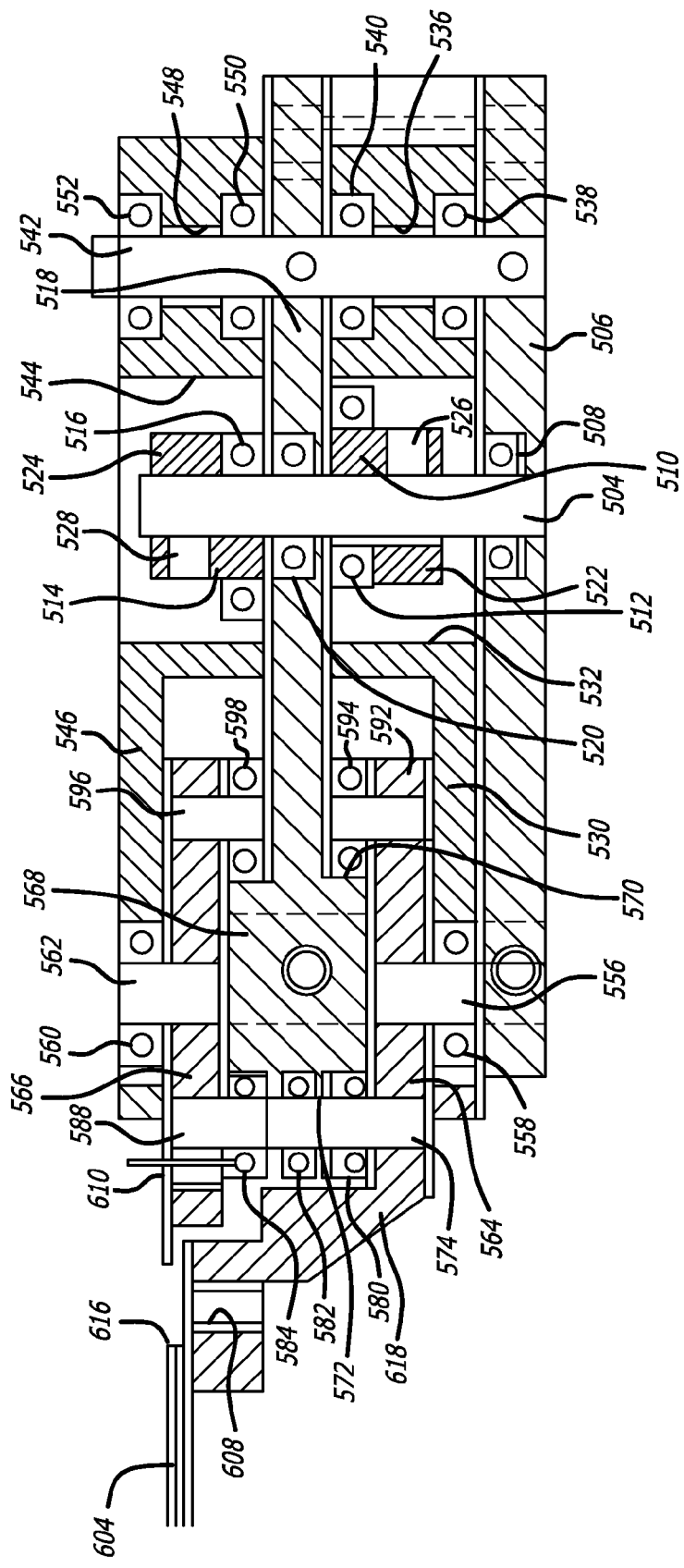
FIG. 26 is a side sectional view of the drive mechanism of FIG. 24.

FIGS. 24, 25 and 26 Saw and Blade Assembly:

The reciprocating mechanism in the FIGS. 24, 25 and 26 saw is different from that for FIGS. 20 and 21 in part because the pivot points for the blades are near the middle of the blades instead of within the housing. FIG. 26 is an enlarged version of the mechanism of FIG. 24. Insofar as some reference numerals would have been too crowded in FIG. 24, that figure does not have all the numerals that FIG. 26 contains. Therefore, one may have to consult both FIGS. 24 and 26 to locate particular numerals.

Motor 502 (only partially shown in FIG. 24) rotates motor shaft 504. The motor shaft extends through bearing 508 in base 506 (FIG. 26). The shaft passes through lower eccentric 510, bearing 520 in central support 518 and upper eccentric 514 (FIG. 26). The eccentrics mount within respective bearings 512 and 516. Rings 522 and 524 position the eccentrics properly along the motor shaft. Set screws in openings 526 and 528 may secure the rings to the shaft.

Bearing 512 and its eccentric mount within opening 532 of lower arm 530. The proximal end of the arm (right side in FIGS. 24, 25 and 26) has a rear bore 536 with a pair of bearings 538 and 540 around the bore. Fixed shaft 542 (FIGS. 24, 25 and 26) extends upward from base 506 through bearings 538 and 540 and through support 518. FIGS. 24 and 26. The mounting permits lower arm 530 to reciprocate about fixed shaft 542. Similarly, bearing 516 and eccentric 514 mount within opening 544 of upper arm 546. The arm's rear end has a rear bore 548 with a pair of bearings 550 and 552. Fixed shaft 542 also extends through bearings 550 and 552. The arrangement allows upper arm 546 to reciprocate about fixed shaft 542.

Rotation of the motor shaft 504 rotates eccentrics 510 and 514. The bearings 512 and 516 in which the eccentrics mount cam against the inside surface of respective openings 532 and 544 and cause lower and upper arms 530 and 546 to reciprocate about fixed shaft 542. Arms 530 and 546 counter-reciprocate about fixed shaft 542 because the eccentrics are 180° out of phase to each other.

As FIG. 25 shows, when the more proximal portion of arms 530 and 546 reciprocate, their distal ends follow and reciprocate. The distance from the distal end of each arm to fixed shaft 542 may be greater than the distance from the motor shaft 504 to fixed shaft 542—about 3:1 in the FIGS. 25 and 26 saw. That geometry causes relatively small movements from the eccentrics acting on their respective arm to yield greater movement of the distal end of each arm.

Near the distal end of each arm 530 and 546, lower distal shaft 556 mounts in bearing 558 and lower traveler 564, and upper distal shaft 562 mounts in bearing 560 and upper traveler 566. See FIGS. 24 and 26. Support 518 may have an enlarged portion 568. The lower traveler is below the bottom of the enlarged portion and the upper traveler is above the enlarged portion in this saw. However, the mechanism could have two supports with one below the lower arm and the other above the upper arm. However, a single support between the arms may produce a more compact mechanism. The enlarged portion has a proximal arcuate surface 570 and a distal arcuate surface 572 (FIGS. 25 and 26). Each arcuate surface is an arc of a circle with a center the pivot point 622 of blades 602 and 604 (left side in FIG. 24).

A pair of pins—only one, 574, is visible in FIG. 26—that are distal to arcuate surface 572 extend upward from lower traveler 564. Bearings 580 and 582 mount on pin 574. The bearings contact and roll on arcuate surface 572 as the distal end of the arm and its traveler reciprocates. Likewise, pins 584 and 586 extend down from upper traveler 566. FIGS. 25 and 26. Bearing 584 mounts on pin 588, and bearing 590 mounts on pin 586. The bearing also contacts arcuate surface 572 to roll as the distal end of the arm and its traveler reciprocate.

Proximal pins 592 and 596 extend from their respective traveler 564 and 566. Each pin has a bearing 594 and 598. The bearings roll along proximal arcuate surface 570 of enlarged portion 568 of central support 518 (FIG. 26). Thus, as FIG. 25 shows, the pins and bearings form a triangle to maintain the upper traveler to the proximal and distal arcuate surfaces 570 and 572 of enlarged portion 568. Consequently, as upper and lower arms 546 and 530 reciprocate, the distal ends of the arms move in arcuate paths about fixed shaft 542.

In FIGS. 24, 25 and 26, bottom and top blades 602 and 604 mount to the lower and upper arms 530 and 546. The mounting is similar to the way the blades attach to the arms in the FIGS. 20 and 21 saw. A clamp (not shown) extends through slot 606 of blade 602 and into bore 608 (FIGS. 26 and 28) to secure the blade to the lower arm. Likewise, bore 610 at the distal end of upper arm 546 aligns with slot 612 in upper blade 604 for receiving a clamp. See FIGS. 24, 25 and 26. Upper blade 604 also has an opening 616 (FIGS. 25, 26 and 27), which is positioned over opening 606 of the lower blade when the blades are assembled to the drive mechanism. Opening 616 allows the clamp to engage the lower blade.

Lower arm 530 has a distal upward bend 618 to position blade 602 properly.

Blades 602 and 604 reciprocate about an axis through the blades at aligned openings 622 through the blades. See FIGS. 24 and 25. A pin 624 extends through the openings to provide a pivot for the blades and to hold the blades together. See the discussion about pin design for the FIGS. 16-19 saw for pin variations for the FIGS. 24 and 25 saw. Having the pivot for the blades along the blades themselves means that as the proximal end of a blade moves in one direction, its distal end pivots in the opposite direction.

Blade 602 has a slot 626 near its distal end, and narrowed region 628 of blade 604 mounts in the slot (FIGS. 24 and 25). Thus, the distal end of lower blade 602 is above the distal end of upper blade 604. The blades are bent at slot 626 and narrowed region 628 (FIG. 24). In this blade assembly, slot 626 is arcuate with its center of curvature at opening 622.

The longitudinal position of opening 622 affects the distance that the cutting edges of the blade move for any movement of the proximal ends of the blades. The length of blade 604 may be about 4.5 in. (11.4 cm). The distance from the cutting surface of blade 604 to the pivot at opening 622 may be 1.75 in. (44 mm), and the distance from the pivot to the proximal end of the blade, which corresponds to arcuate surface 572, may be about 2.75 in. (70 mm).

Dimensions of the components in FIGS. 24, 25 and 26 can vary. Some components in FIGS. 24, 25 and 26 have the following dimensions. Lower arm 530 may be 1.94 in. (49.2 mm) long and 0.19 in. (5.8 mm) thick. The proximal end may be 0.5 in. (12.7 mm) wide and the distal end may be 0.75 in. (19 mm) wide. Upper arm 546 has similar width dimensions. It may be 1.47 in. (37.3 mm) long and 0.22 in. (5.56 mm) thick. The distal portion may be slightly thinner.

Support 518 may be 0.25 in. (6.4 mm) thick over most of its 3.25 in. (82.6 mm) length. However, enlarged portion 568 may be 0.5 in. (12.7 mm) thick. A short, narrower portion may connect the enlarged portion to the proximal end of the support. Eccentrics 510 and 514 are offset 0.06 in. (1.6 mm) from the centerline of the motor shaft 504. The blades are 0.025 in. (0.6 mm) thick so that their combined width may be 0.05 in. (1.3 mm).

Figure 27:
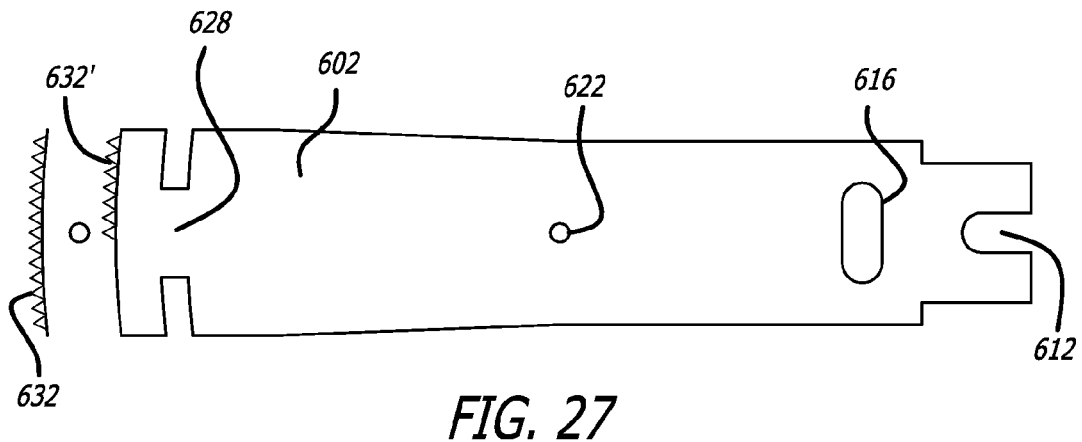
FIGS. 27 and 28 are plan views of blades that may be used in the saw and blade assembly of FIGS. 24, 25 and 26.
Figure 28:
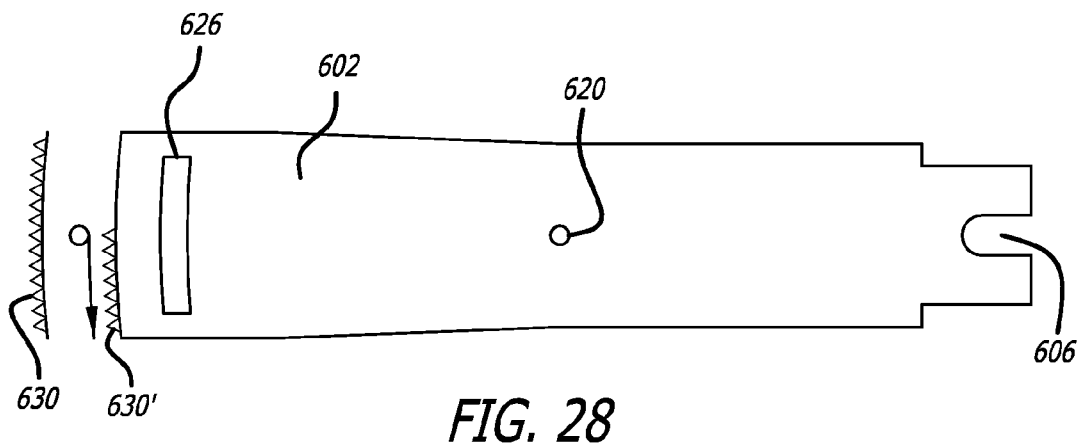

FIGS. 27 and 28 show alternative blade serrations. They can extend over the entire cutting surface, or they may extend only over half or some smaller distance less than the full width. FIGS. 27 and 28 have alternatives in which cutting surface 630' on blade 602 is on one side of the blade and cutting surface 632' on blade 604 is on the opposite side. Other blade assemblies would accept similar cutting blade configurations.

Figure 29:
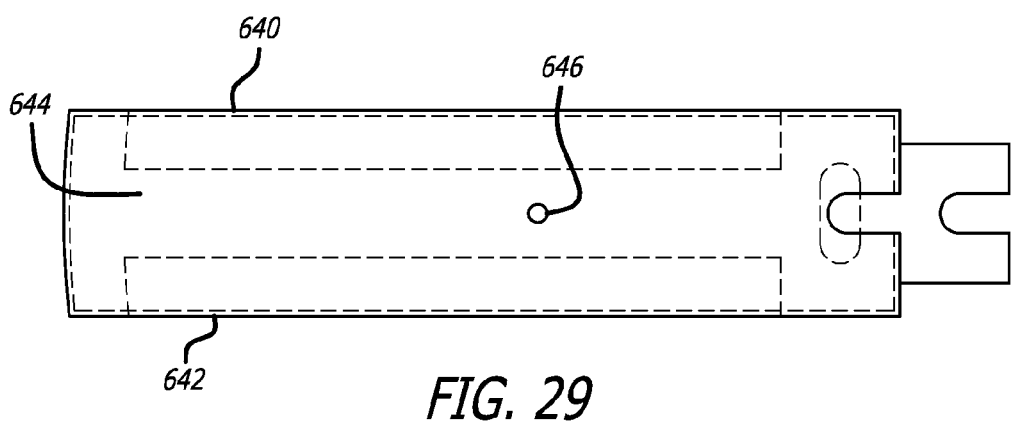
FIG. 29 is a plan view of another blade assembly that can be used with the FIGS. 24, 25 and 26 saw and blade assembly.

FIG. 29 Blade Assembly:

FIG. 29 shows a three-blade version. Two outside blades 640 and 642 reciprocate together in one direction while inside blade 644 reciprocates in the opposite direction. The two outside blades attach to the same arm and the inside blade attaches to the other arm. They reciprocate about axis 646. This blade assembly works with the FIGS. 24, 25 and 26 saw. However, three-blade assemblies could be modified to work with the other saws. The outside blades may be about half the thickness of blades of FIGS. 27 and 28, about 0.013 in. (0.3 mm) to keep the three-blade assembly blades about the same thickness as the other twoblade assemblies.

Figure 30:
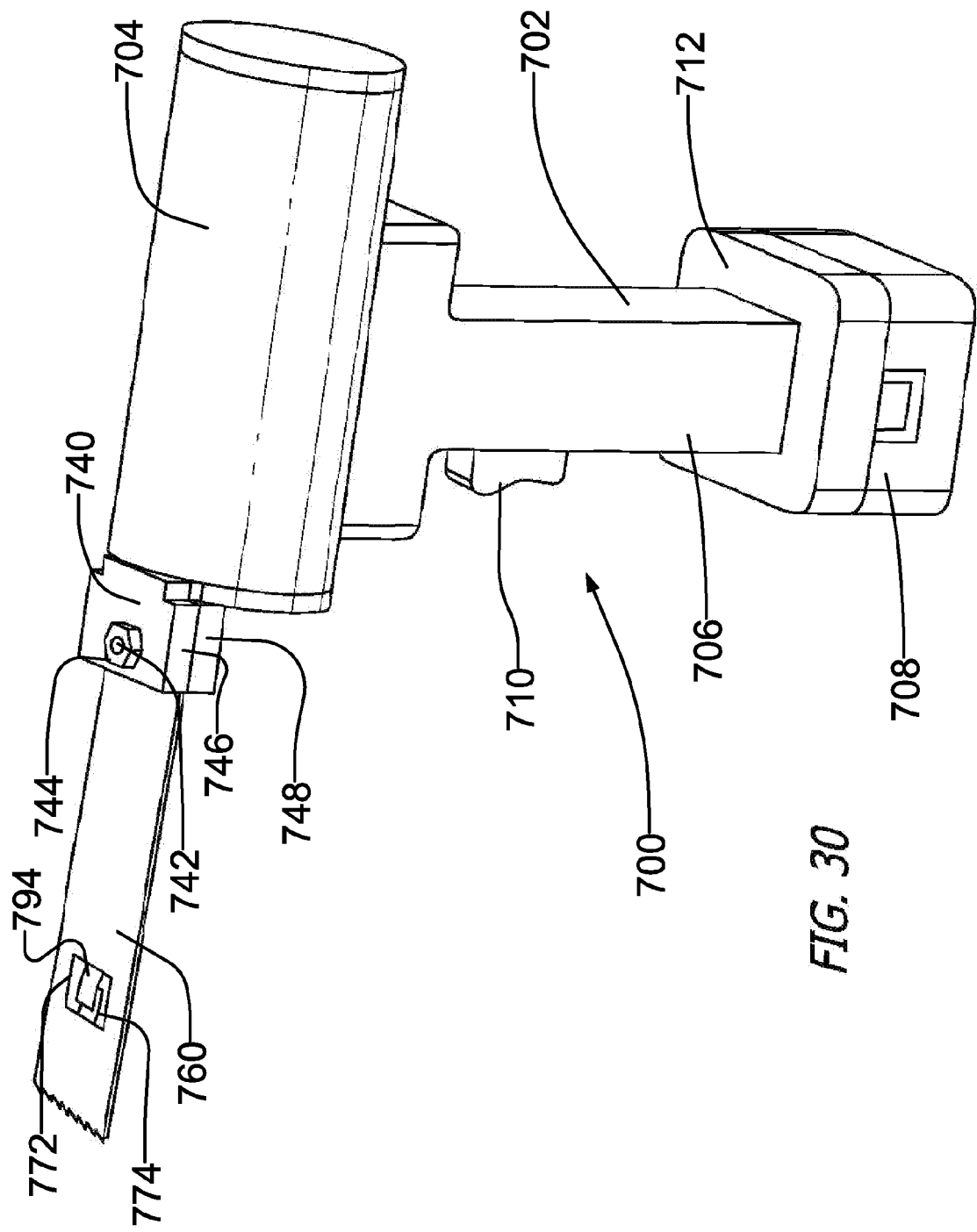
FIG. 30 is a perspective view of another saw.
Figure 31:
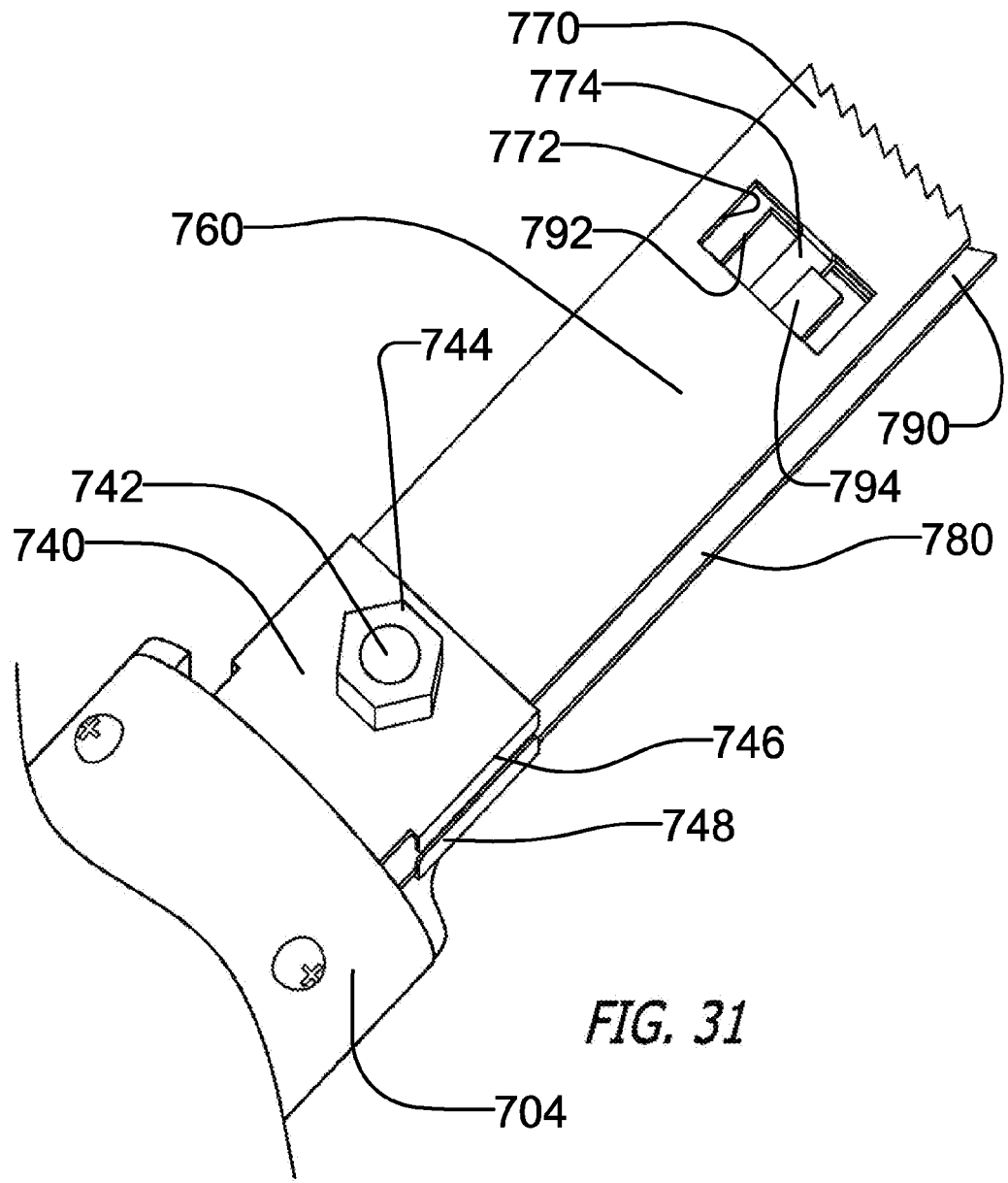
FIG. 31 is a perspective view of the blade assembly attached to the saw in FIG. 30.

FIGS. 30 through 33 Saw and Blade Assembly:

The blades shown in FIGS. 31, 32 and 33 may attach to saw shown in FIG. 30. However, those blades may work with other saws, or they may be modified for other saws. Saw 700 may be pistol-shaped as shown in FIG. 30. The saw includes motor housing 702 that mounts an internal motor (now shown) and another or drive housing 704. The drive housing contains a mechanism such as one described elsewhere in this application that counter-reciprocates blades 760 and 780 or other appropriate blades.

FIG. 30 shows a sharp divide between motor housing 702 and drive housing 704, but the housings could be designed with a smooth transition between them.

Housing 702 forms the handle 706 of the pistol-shaped saw. Battery 708 attaches to base 712 of the handle. The battery may be one that powers cordless tools such as drills and portable tools. Makita, Black & Decker, Craftsman and others sell them. The batteries may be NiMH, but lithium-ion batteries also are common. Voltages also vary. These types of batteries may be removed from the handle for recharging or replacement. Powering the saw with battery power makes the saw portable and more maneuverable. However, the saw could connect to available AC or DC power.

The saw's shape may vary with changes to motor and drive housings 702 and 704 or for other reasons. The housing may be metal such as aluminum or stainless steel, but plastic housing parts may replace some or all of the metal ones. Any chosen material should be capable of withstanding the high temperature of autoclaving. Likewise, internal parts need to withstand the same high temperatures.

Handle 706 includes spring-loaded trigger switch 710 that controls the saw's motor. Other controls could be used. The trigger switch may control a motor controller (not shown) to control the motor speed. Otherwise, it can be an on/off switch.

Counter-reciprocating blades 760 and 780 project from the front end of motor housing 704. See FIG. 30. Thus, with the blades in their positions shown in FIG. 30, the blades project toward bone or other tissue. From that initial position, the surgeon can maneuver the saw to position the saw blades in the proper orientation toward the particular tissue being cut.

The mechanisms previously described in this application can reciprocate the blade, and other mechanisms for converting rotary motion from the motor into blade reciprocation can be used. Nevertheless, mechanism driven from vertically mounted motor shafts such as those of FIGS. 6 and 8 usually are less complex than those driven by a motor with a horizontally mounted shaft.

The saw may use blades similar to those shown in FIGS. 7, 9, 10, 22 and 23 (ignoring the attachment structure). The axis of pivoting is within drive housing 704 and is proximal to the blade's proximal end. For example, the axis for pivoting is through shafts 234 in FIG. 6 or 294 in FIG. 8.

FIGS. 30 through 33 show another blade design. Upper blade 760 and lower blade 780 are of equal length. Blade 760 and 780 may be 1/32 in. (0.7 mm) thick for a total thickness when two blades are superimposed of 1/16 in. (1.4 mm). The length excluding the proximal ends may be 3.5 in. (78.4 mm), and the total length may be 4.5 in. (100.8 mm).

The blades are about 1.0 in. (24 mm) wide although their proximal ends 762, 782 (FIGS. 32 and 33) are 0.745 in. (18.9 mm) wide to fit into blade holder 740 (FIGS. 30 and 31). The blade holder may have walls 746 and 748 (FIGS. 30 and 31) that engage the edges of the proximal ends of the blade to help secure the blades to the blade holder as the blade holder counter-reciprocate.

The blades also may have indicia (not shown) to show the depth of cut or other information.

Each blade has a bend 764, 784 (FIG. 33) near its proximal end. The bend spaces the respective proximal ends from each other in the particular blade holder 740 in FIGS. 30 and 31. The spacing may help the sides of the blades' proximal ends engage the sidewalls and other structure of the blade holder.

Each proximal end 762, 782 has a slot 766 and a circular opening 768 at the distal end of the slot. See FIG. 31, which only shows the slot and opening in upper blade 760. Bolt 742 extends through blade holder 740 and the circular openings. Tightening nut 744 of the bolt secures the bolt and the blade holder to the blades. The blade slots may be wide enough to slide past bolt 742 when the nut is loose. Thus, removing the nut completely from the blade holder may not be necessary, a benefit when replacing blades quickly.

Though FIGS. 30 and 31 uses a nut and bolt, other fasteners including quick-release ones such as those described previously could replace the nut and bolt.

Keeping the bottom surface of top blade 760 against the top surface of bottom blade 780 during reciprocation is desirable. By controlling bends 764, 784 and the surfaces of blade holder 740, the distal ends 770, 790 of the blade may push against each other. However, additional structure including those described previously may hold the blades together.

Each blade in FIGS. 30 through 33 may have a lateral slot 772, 792 (FIGS. 32 and 33), which are aligned with each other. A short, bent projection extends longitudinally into each slot. Projection 774 of blade 760 (FIG. 33) extends distally from the proximal wall of slot 772. Because the projection is bent, the projection extends into slot 792 of blade 780. Similarly, projection 794 of blade 780 extends from the distal end of slot 792. Because the projection is bent, the projection extends into slot 772 of blade 760.

Projections 774 and 794 contact each other and urge the distal portions of blades 760 and 780 together. The flat surfaces of the projections slide relative to each other as the blades reciprocate. Accordingly, lateral slots 772, 792 must be wide enough to accommodate the relative movement of the projections as the blade counter-reciprocate. Likewise, the projections must be wide enough to remain engaged during blade reciprocation. In addition, the blades could be designed such that projection 774 of blade 760 extends proximally into slot 772, and projection 794 of blade 780 extends distally into slot 792.

Blades 760 and 780 may have openings—FIG. 32 shows two circular openings 776, 778 in blade 760—for debris to pass from between the blades.

FIG. 31 shows serrations 778 on the distal surface of blade 760. Blade 780 has complimentary serrations. The serrations of blade 760 in FIG. 31 are arranged to cut in one direction primarily, and the complimentary serrations on blade 780 are arranged to cut in the opposite direction primarily. However, half the serrations on each blade could point differently so that the blades cut in both directions.

Closing Comments:

Throughout this description, the embodiments and examples shown should be considered as exemplars rather than limitations on the apparatus and procedures disclosed or claimed. Although many of the examples involve specific combinations of method acts or system elements, it should be understood that those acts and those elements may be combined in other ways to accomplish the same objectives. With regard to flowcharts, additional and fewer steps may be taken, and the steps as shown may be combined or further refined to achieve the described methods. Acts, elements and features discussed only in connection with one embodiment are not intended to be excluded from a similar role in other embodiments.

As used in this application, "plurality" means two or more. A "set" of items may include one or more of such items. Whether in the written description or the claims, the terms "comprising," "including," "carrying," "having," "containing," "involving," and the like are to be understood to be open-ended, i.e., to mean including but not limited to. Only the transitional phrases "consisting of" and "consisting essentially of," respectively, are closed or semi-closed transitional phrases with respect to claims. Use of ordinal terms such as "first," "second," "third," etc., in the claims to modify a claim element does not by itself connote any priority, precedence or order of one claim element over another or the temporal order in which acts of a method are performed. These terms are used merely as labels to distinguish one claim element having a certain name from another element having a same name (but for use of the ordinal term) to distinguish the claim elements. As used in this application, "and/or" means that the listed items are alternatives, but the alternatives also include any combination of the listed items.

I claim:

1. A blade assembly for use in a counter-reciprocating saw comprising a first blade and a second blade; each blade having a proximal end attachable to a mechanism for reciprocating the blades in opposite directions relative to each other; each blade also having a distal end and a cutting surface at the distal end; wherein the proximal end of the first blade is above the proximal end of the second blade and the distal end of the first blade is below the proximal end of the second blade.

2. The blade assembly of claim 1, wherein one of the blades has a slot and a portion of the other blade extends through the slot.

3. The blade assembly of claim 2, wherein the first and second blades have an axis of reciprocation about which the blades reciprocate and wherein the slot conforms to an arc of a circle that has an axis at the axis of reciprocation.

4. The blade assembly of claim 3, wherein the slot on one of the blades is wide enough in the direction of the arc to accommodate movement of the other blade reciprocating in the slot while the blades counter-reciprocate.

5. The blade assembly of claim 1, further comprising a pin extending through the first and second blades, the pin positioning the blades relative to each other.

6. The blade assembly of claim 5, wherein the pin has two heads, each blade having a countersunk portion for receiving one of the heads of the pin.

7. The blade assembly of claim 1, wherein the first and second blades have an axis of reciprocation about which the blades reciprocate, the blade assembly further comprising a pin extending through the first and second blades at the axis of reciprocation.

8. The blade assembly of claim 1, wherein the first blade has a region into which a region of the second blade extends when the first and second blades are assembled together, the region of the first blade being sized to accommodate reciprocation of the region of the second blade within the region as the second blade counter-reciprocates relative to the first blade.

9. The blade assembly of claim 1, wherein the second blade has a cutting plane, a cutout section and a plateau member spanning the sides of the cutout section, the plateau member being in a plane spaced from the cutting plane, the plateau member being received within the cutout of the first blade.

10. The blade assembly of claim 1, wherein one of the blades has a slot and a portion of the other blade extends through the slot, the blade containing the slot having lateral extensions adjacent the slot along which the blade that extends through the slot can slide.

11. The blade assembly of claim 1, wherein one of the blades has a cutting plane, a cutout section and a plateau member spanning the sides of the cutout section, the plateau member being in a plane spaced from the cutting plane, the plateau member being received within the cutout of the first blade.

12. The blade assembly of claim 1, wherein at least one of the blades has at least one slot spaced from and adjacent the distal end of the blade.

13. The blade assembly of claim 1, further comprising a third blade in the plane of the first and second blade.

14. A blade assembly for use in a counter-reciprocating saw comprising:
   a) a first blade and a second blade, each blade having a proximal portion and a distal portion, the distal portion having a cutting region;
   b) the first blade having a slot; and
   d) the second blade near the distal portion including a bent portion extending through the slot.

15. The blade assembly of claim 14, wherein the first and second blades have an axis of reciprocation about which the blades reciprocate and wherein the slot conforms to an arc of a circle that has an axis at the axis of reciprocation.

16. The blade assembly of claim 14, further comprising a pin extending through the first and second blades, the pin positioning the first and second blades relative to each other.

17. The blade assembly of claim 14, wherein the first blade has a region into which a region of the second blade extends when the first and second blades are assembled together, the region of the first blade being sized to accommodate reciprocation of the region of the second blade within the region as the second blade counter-reciprocates relative to the first blade.

18. The blade assembly of claim 14, further comprising an arm assembly on each blade, one of the blades having a cutout section, the arm assembly of the blade extending through the cutout section and being attached to a portion of the blade, the second blade having a cutout section and a plateau member spanning the sides of the cutout and in a plane spaced from the plane of the second blade, the plateau member being received within the cutout of the first blade.

19. The blade assembly of claim 18, wherein the plateau member of the second blade reciprocates within the cutout of the first blade without contacting the sides of the cutout of the first blade, the arm assembly of the first blade reciprocating in the space below the plateau member.

20. The blade assembly for use in a counter-reciprocating saw of claim 14 wherein the first blade is bent at the bent portion of the second blade.

21. A blade assembly for use in a counter-reciprocating saw comprising:
   a) a first blade and a second blade, each blade having a proximal portion and a distal portion, each blade having a cutting region at its distal portion;
   b) the first blade having a slot; and
   c) the second blade having a bent portion adjacent the slot in the first blade, the second blade further comprising a narrow portion extending through the slot.

22. The blade assembly of claim 21 further comprising at least one opening adjacent the cutting region.

23. The blade assembly of claim 22 wherein the opening of the first blade is between the slot and the cutting region of at least one of the blades.

24. The blade assembly for use in a counter-reciprocating saw of claim 21 wherein the narrow portion of the second blade is bent at an angle to extend through the slot of the first blade.

25. A blade assembly for use in a counter-reciprocating saw comprising a top blade and a bottom blade; each blade having a proximal end attachable to a mechanism for reciprocating the blades in opposite directions relative to each other; each blade also having a distal end and a cutting surface at the distal end; each blade having a slot between the proximal and distal end of the blade; each blade having a projection bent to extend into the slot of the other blade, wherein the projection of the top blade extends below the projection of the bottom blade, whereby the projections can slide relative to each other as the blades counter-reciprocate.

* * * * *